(12) United States Patent
Imai

(10) Patent No.: US 12,419,615 B2
(45) Date of Patent: Sep. 23, 2025

(54) ACOUSTIC WAVE DIAGNOSTIC APPARATUS AND METHOD OF CONTROLLING ACOUSTIC WAVE DIAGNOSTIC APPARATUS

(71) Applicant: FUJIFILM Corporation, Tokyo (JP)

(72) Inventor: Yoshiro Imai, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 736 days.

(21) Appl. No.: 17/134,887

(22) Filed: Dec. 28, 2020

(65) Prior Publication Data
US 2021/0113196 A1    Apr. 22, 2021

Related U.S. Application Data

(63) Continuation of application No. PCT/JP2019/020018, filed on May 21, 2019.

(30) Foreign Application Priority Data

Jul. 2, 2018 (JP) ................................. 2018-126175

(51) Int. Cl.
  *A61B 8/00* (2006.01)
  *G06F 3/041* (2006.01)
  *G06F 3/0488* (2022.01)

(52) U.S. Cl.
  CPC ............... *A61B 8/54* (2013.01); *A61B 8/465* (2013.01); *A61B 8/469* (2013.01); *G06F 3/041* (2013.01);
  (Continued)

(58) Field of Classification Search
  CPC ............. G06T 2207/10132; G06T 7/62; G06T 7/0012; G06T 7/12; G06T 2207/10016;
  (Continued)

(56) References Cited

U.S. PATENT DOCUMENTS 11,170,519 B2 * 11/2021 Ebata ................... A61B 8/5223
11,636,616 B2 *  4/2023 Ebata ........................ G06T 7/60
                                                            382/128

(Continued)

FOREIGN PATENT DOCUMENTS

CN         101951840 A     1/2011
CN         104799882 A     7/2015
(Continued)

OTHER PUBLICATIONS

"UCSF ED Liver and Gallbladder/Biliary Ultrasound Protocol" Jun. 22, 2018 (retrieved from https://web.archive.org/web/20180622004923/https://edus.ucsf.edu/sites/edus.ucsf.edu/files/wysiwyg/UCSF%20ED%20US%20Protocol%20Biliary_Final.pdf) (Year: 2018).*

(Continued)

*Primary Examiner* — Keith M Raymond
*Assistant Examiner* — Johnathan Maynard
(74) *Attorney, Agent, or Firm* — Studebaker Brackett PLLC

(57) ABSTRACT

An ultrasound diagnostic apparatus 1 includes a display unit 8, an operating unit 15, a measurement position designation reception unit 14 that receives designation of a measurement position on an ultrasound image from a user through the operating unit 15, a measurement target recognition unit 9 that recognizes a measurement target included in the ultrasound image of a recognition range decided based on the received measurement position, a measurement algorithm setting unit 12 that sets a measurement algorithm based on the recognized measurement target, and a measurement unit 10 that measures the measurement target based on the set measurement algorithm and displays a measurement result on the display unit 8.

19 Claims, 16 Drawing Sheets

(52) U.S. Cl.
CPC .. *G06F 3/0488* (2013.01); *G06F 2203/04105* (2013.01)

(58) Field of Classification Search
CPC ... G06T 7/20; G06T 7/60; G06T 11/60; G06T 2200/24; G06T 2207/20081; G06T 2207/20084; G06T 2207/20221; G06T 2207/30004; G06T 2207/30008; G06T 2207/30044; G06T 2207/30048; A61B 8/463; A61B 8/5223; A61B 5/1075; A61B 8/465; A61B 8/469; A61B 8/5207; A61B 8/14; A61B 8/085; A61B 8/462; A61B 5/0095; A61B 8/0891; A61B 5/0035; A61B 5/7425; A61B 8/08; A61B 8/0833; A61B 8/0866; A61B 8/0875; A61B 8/0883; A61B 8/4272; A61B 8/4416; A61B 8/4444; A61B 8/46; A61B 8/461; A61B 8/467; A61B 8/468; A61B 8/486; A61B 8/5261; A61B 8/5284; G06V 10/25; G06V 10/248; G06V 2201/03; G06F 3/04845; G16H 50/30
See application file for complete search history.

(56) References Cited

U.S. PATENT DOCUMENTS

| | | | |
|---|---|---|---|
| 2006/0274928 A1* | 12/2006 | Collins | G16H 30/40 382/132 |
| 2008/0267499 A1* | 10/2008 | Deischinger | G06V 10/25 382/173 |
| 2010/0322495 A1 | 12/2010 | Collet-Billon et al. | |
| 2011/0004100 A1 | 1/2011 | Iimura | |
| 2015/0138116 A1* | 5/2015 | Lee | G06F 3/0484 345/173 |
| 2015/0213597 A1 | 7/2015 | Oh et al. | |
| 2015/0320399 A1* | 11/2015 | Chono | G16H 50/30 382/131 |
| 2016/0042525 A1 | 2/2016 | Lee et al. | |
| 2016/0085328 A1 | 3/2016 | Lee et al. | |
| 2016/0361043 A1 | 12/2016 | Kim et al. | |
| 2017/0007161 A1* | 1/2017 | Zou | A61B 5/1075 |
| 2019/0148011 A1* | 5/2019 | Rao | G16H 50/20 600/437 |
| 2019/0236330 A1* | 8/2019 | Miyoshino | G06T 7/00 |
| 2020/0178933 A1* | 6/2020 | Imai | A61B 8/462 |
| 2021/0077066 A1* | 3/2021 | Imai | A61B 8/467 |

FOREIGN PATENT DOCUMENTS

| | | | | |
|---|---|---|---|---|
| EP | 3308714 A1 * | 4/2018 | | G16H 50/30 |
| JP | 2010-148811 A | 7/2010 | | |
| JP | 2013-111434 A | 6/2013 | | |
| JP | 2017-164077 A | 9/2017 | | |
| WO | WO-2017216238 A1 * | 12/2017 | | A61B 5/0077 |

OTHER PUBLICATIONS

The extended European search report issued by the European Patent Office on Jul. 30, 2021, which corresponds to European Patent Application No. 19831559.0-1126 and is related to U.S. Appl. No. 17/134,887.

International Search Report issued in PCT/JP2019/020018; mailed Aug. 20, 2019.

International Preliminary Report on Patentability and Written Opinion issued in PCT/JP2019/020018; issued Jan. 5, 2021.

An Office Action mailed by China National Intellectual Property Administration on Nov. 11, 2023, which corresponds to Chinese Patent Application No. 201980044574.X and is related to U.S. Appl. No. 17/134,887; with English language translation.

An Office Action mailed by the European Patent Office on Mar. 21, 2024, which corresponds to European Patent Application No. 19831559.0 and is related to U.S. Appl. No. 17/134,887.

* cited by examiner

ACOUSTIC WAVE DIAGNOSTIC APPARATUS AND METHOD OF CONTROLLING ACOUSTIC WAVE DIAGNOSTIC APPARATUS

CROSS-REFERENCE TO RELATED APPLICATIONS

This application is a Continuation of PCT International Application No. PCT/JP2019/020018 filed on May 21, 2019, which claims priority under 35 U.S.C. § 119(a) to Japanese Patent Application No. 2018-126175 filed on Jul. 2, 2018. The above application is hereby expressly incorporated by reference, in its entirety, into the present application.

BACKGROUND OF THE INVENTION

1. Field of the Invention

The present invention relates to an acoustic wave diagnostic apparatus and a method of controlling an acoustic wave diagnostic apparatus, and in particular, to an acoustic wave diagnostic apparatus and a method of controlling an acoustic wave diagnostic apparatus that measure a part on an acoustic wave image.

2. Description of the Related Art

In recent years, a medical acoustic wave diagnostic apparatus generally has a measurement function of measuring a length, a size, an area, and the like of various organs, lesions, and the like included in an acquired acoustic wave image. In order to measure a measurement target, normally, a user operates a caliper, that is, a cursor using an input device that inputs coordinates, such as a touch pad, a trackball, or a mouse, and sets a measurement point, a region of interest, or the like on a display image. In this case, in a case where a manual operation of the user is performed, an experience, proficiency, or the like of the user affects, various attempts have been made to automate the operation.

For example, JP2013-111434A discloses an ultrasound diagnostic apparatus that, in a case where a position of a caliper for use in measuring a measurement target is input from a user through an operating unit on an ultrasound image, corrects the position of the caliper to an appropriate position by executing image processing on a peripheral region of the input caliper. In the ultrasound diagnostic apparatus disclosed in JP2013-111434A, for example, in a case where a pair of calipers for measuring a distance between two points on the ultrasound image is input by the user, a pair of calipers is corrected to appropriate positions, and a length of the measurement target is measured based on a pair of corrected calipers.

SUMMARY OF THE INVENTION

However, in the ultrasound diagnostic apparatus disclosed in JP2013-111434A, in measuring the measurement target, since the calipers need to be manually input by the user through an operating unit, there is a problem in that the user is required to spend much labor.

The invention has been accomplished in order to solve such a problem in the related art, and an object of the invention is to provide an acoustic wave diagnostic apparatus and a method of controlling an acoustic wave diagnostic apparatus capable of conveniently executing measurement.

In order to achieve the above-described object, the invention provides an acoustic wave diagnostic apparatus comprising a display unit that displays an acquired acoustic wave image, an operating unit through which a user performs an input operation, a measurement position designation reception unit that receives designation of a measurement position on the acoustic wave image displayed on the display unit from the user through the operating unit, a measurement target recognition unit that recognizes a measurement target included in the acoustic wave image of a recognition range decided based on the measurement position received by the measurement position designation reception unit, a measurement algorithm setting unit that sets a measurement algorithm based on the measurement target recognized by the measurement target recognition unit, and a measurement unit that measures the measurement target on the acoustic wave image based on the measurement algorithm set by the measurement algorithm setting unit and displays a measurement result on the display unit.

It is preferable that, in a case where the measurement position is received by the measurement position designation reception unit, the recognition of the measurement target by the measurement target recognition unit, the setting of the measurement algorithm by the measurement algorithm setting unit, and the measurement and the display of the measurement result by the measurement unit are automatically performed sequentially.

Alternatively, the acoustic wave diagnostic apparatus may further comprise a measurement execution instruction reception unit that receives an instruction to start the measurement of the measurement target issued by the user through the operating unit, and in a case where the instruction to start the measurement of the measurement target is received by the measurement execution instruction reception unit, the recognition of the measurement target by the measurement target recognition unit, the setting of the measurement algorithm by the measurement algorithm setting unit, and the measurement and the display of the measurement result by the measurement unit may be automatically performed sequentially.

In a case where a plurality of the measurement targets are recognized in the recognition range by the measurement target recognition unit, the measurement algorithm setting unit may set the measurement algorithm for each of the plurality of the measurement targets, and the measurement unit may measure each of the plurality of the measurement targets and may display a measurement result of each measurement target on the display unit.

In this case, the measurement unit may display the measurement results of the plurality of the measurement targets on the display unit in association with the plurality of the measurement targets on the acoustic wave image, respectively.

The acoustic wave diagnostic apparatus may further comprise a measurement order decision unit that, in a case where a plurality of the measurement targets are recognized in the recognition range by the measurement target recognition unit, decides a measurement order of the plurality of the measurement targets, the measurement algorithm setting unit may set the measurement algorithm sequentially for the plurality of the measurement targets in compliance with the measurement order decided by the measurement order decision unit, and the measurement unit may measure the measurement targets sequentially from the measurement target, for which the measurement algorithm is set by the measurement algorithm setting unit, and may display measurement results of the plurality of the measurement targets on the display unit.

In this case, the measurement order decision unit may provide the measurement order to the plurality of the measurement targets such that the shorter a distance from the measurement position on the acoustic wave image is, the earlier the measurement order becomes.

Alternatively, the acoustic wave diagnostic apparatus may further comprise a measurement target selection reception unit that, in a case where a plurality of the measurement targets are recognized in the recognition range by the measurement target recognition unit, receives selection of one measurement target among the plurality of the measurement targets from the user through the operating unit, the measurement algorithm setting unit may set the measurement algorithm based on the one measurement target of which the selection is received by the measurement target selection reception unit, and the measurement unit may measure the one measurement target based on the measurement algorithm and may display a measurement result on the display unit.

The operating unit may include a touch sensor disposed to be superimposed on the display unit, and the measurement position designation reception unit may receive a position touched with a finger of the user on the acoustic wave image displayed on the display unit as the measurement position.

The recognition range may have a determined size.

Alternatively, the acoustic wave diagnostic apparatus may further comprise a recognition range decision unit that sets the size of the recognition range according to a touch operation with the finger of the user.

In this case, the recognition range decision unit may set the size of the recognition range according to a length of a time for which the measurement position on the acoustic wave image is touched with the finger of the user.

The recognition range decision unit may set the size of the recognition range according to a movement direction and a movement distance of the finger of the user on the acoustic wave image in a case where the measurement position of the acoustic wave image is touched with the finger of the user and the finger of the user is moved on the acoustic wave image.

The operating unit may include a pressure sensor disposed to be superimposed on the display unit and the touch sensor, and the recognition range decision unit may set the size of the recognition range according to magnitude of pressure of the finger of the user detected by the pressure sensor.

The invention provides a method of controlling an acoustic wave diagnostic apparatus comprising displaying an acquired acoustic wave image, receiving user's designation of a measurement position on the acoustic wave image, deciding a recognition range on the acoustic wave image based on the received measurement position, recognizing a measurement target included in the decided recognition range, setting a measurement algorithm based on the recognized measurement target, measuring the measurement target from the acoustic wave image based on the set measurement algorithm, and displaying a measurement result of the measurement target.

According to the invention, the acoustic wave diagnostic apparatus comprises the operating unit through which the user performs the input operation, the measurement position designation reception unit that receives designation of the measurement position on the acoustic wave image displayed on the display unit from the user through the operating unit, the recognition range decision unit that decides the recognition range on the acoustic wave image based on the measurement position received by the measurement position designation reception unit, the measurement target recognition unit that recognizes the measurement target included in the acoustic wave image of the recognition range decided by the recognition range decision unit, the measurement algorithm setting unit that sets the measurement algorithm based on the measurement target recognized by the measurement target recognition unit, and a measurement unit that measures the measurement target on the acoustic wave image based on the measurement algorithm set by the measurement algorithm setting unit and displays a measurement result on the display unit. Thus, it is possible to conveniently execute measurement.

DESCRIPTION OF THE PREFERRED EMBODIMENTS

Hereinafter, embodiments of the invention will be described referring to the accompanying drawings.

Embodiment 1

Figure 1:
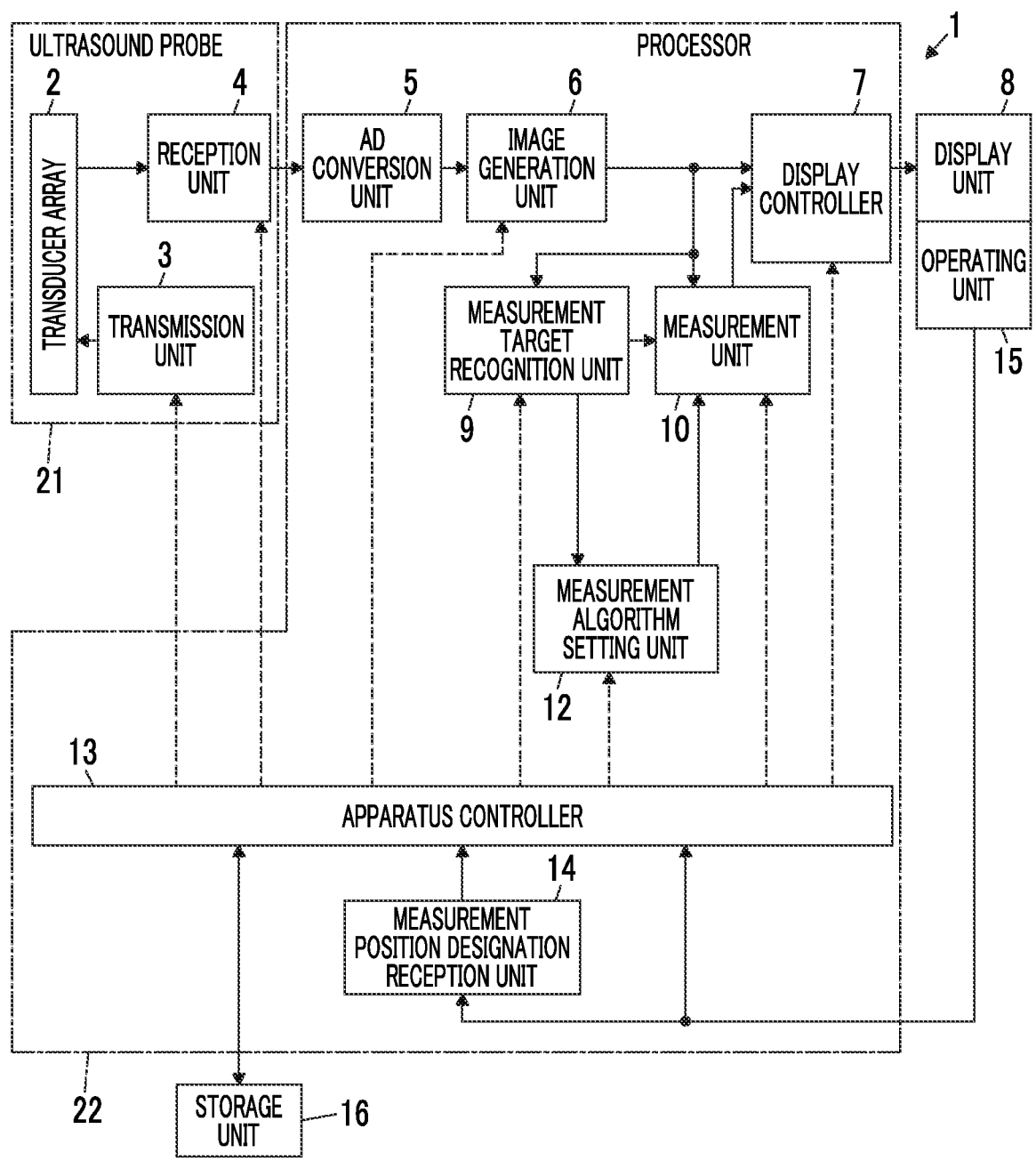
FIG. 1 is a block diagram showing the configuration of an ultrasound diagnostic apparatus according to Embodiment 1 of the invention.

FIG. 1 shows the configuration of an ultrasound diagnostic apparatus 1 according to Embodiment 1 of the invention. As shown in FIG. 1, the ultrasound diagnostic apparatus 1 comprises a transducer array 2, and a transmission unit 3 and a reception unit 4 are connected to the transducer array 2. An analog-to-digital (AD) conversion unit 5, an image generation unit 6, a display controller 7, and a display unit 8 are connected sequentially to the reception unit 4, and an operating unit 15 is disposed to be superimposed on the display unit 8. A measurement target recognition unit 9 and a measurement unit 10 are connected to the image generation unit 6, the measurement unit 10 is connected to the measurement target recognition unit 9, and the display controller 7 is connected to the measurement unit 10. A measurement algorithm setting unit 12 is connected to the measurement target recognition unit 9, and the measurement unit 10 is connected to the measurement algorithm setting unit 12.

An apparatus controller 13 is connected to the transmission unit 3, the reception unit 4, the image generation unit 6, the display controller 7, the measurement target recognition unit 9, the measurement unit 10, and the measurement algorithm setting unit 12, and a measurement position designation reception unit 14, the operating unit 15, and a storage unit 16 are connected to the apparatus controller 13.

The transducer array 2, the transmission unit 3, and the reception unit 4 configure an ultrasound probe 21, and the AD conversion unit 5, the image generation unit 6, the display controller 7, the measurement target recognition unit 9, the measurement unit 10, the measurement algorithm setting unit 12, the apparatus controller 13, and the measurement position designation reception unit 14 configure a processor 22.

The transducer array 2 of the ultrasound probe 21 shown in FIG. 1 has a plurality of ultrasound transducers arranged in a one-dimensional or two-dimensional manner. The ultrasound transducers transmit ultrasonic waves in compliance with drive signals supplied from the transmission unit 3, receive reflected waves from a subject, and output reception signals. Each ultrasound transducer is constituted by forming electrodes at both ends of a piezoelectric body made of, for example, piezoelectric ceramic represented by lead zirconate titanate (PZT), a polymer piezoelectric element represented by poly vinylidene di fluoride (PVDF), piezoelectric single crystal represented by lead magnesium niobate-lead titanate (PMN-PT), or the like.

The transmission unit 3 of the ultrasound probe 21 includes, for example, a plurality of pulse generators, and adjusts a delay amount of each drive signal based on a transmission delay pattern selected according to a control signal from the apparatus controller 13 such that the ultrasonic waves transmitted from a plurality of ultrasound transducers of the transducer array 2 form an ultrasonic beam, and supplies the drive signals to a plurality of ultrasound transducers. In this way, in a case where a pulsed or continuous-wave voltage is applied to the electrodes of each of the ultrasound transducers of the transducer array 2, the piezoelectric body expands and contracts to generate a pulsed or continuous-wave ultrasonic wave from each of the ultrasound transducers. An ultrasonic beam is formed from a combined wave of the ultrasonic waves.

The transmitted ultrasonic beam is reflected by, for example, a target, such as a part of the subject, and propagates toward the transducer array 2 of the ultrasound probe 21. The ultrasonic waves that propagate toward the transducer array 2 in this way are received by the respective ultrasound transducers configuring the transducer array 2. In this case, each of the ultrasound transducers configuring the transducer array 2 expands and contracts with reception of a propagating ultrasound echo to generate an electrical signal, and outputs the electrical signal to the reception unit 4 as a reception signal. Though not shown, the reception unit 4 has an amplification unit that amplifies the reception signal input from each of the ultrasound transducers, and a signal amplified by the amplification unit is sent to the AD conversion unit 5.

The AD conversion unit 5 of the processor 22 converts the reception signal sent from the reception unit 4 into digitized element data, and sends the element data to the image generation unit 6.

Figure 2:
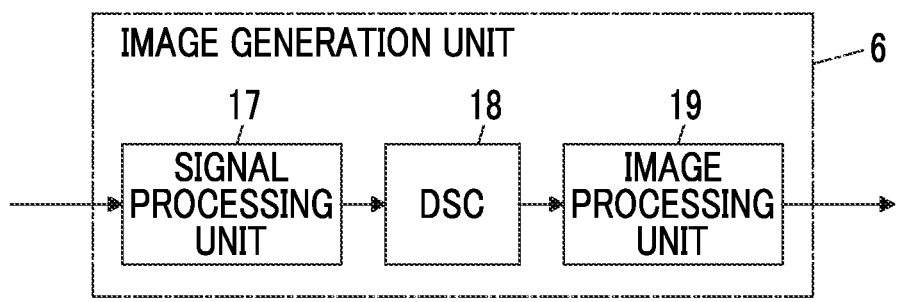
FIG. 2 is a block diagram showing the internal configuration of an image generation unit in Embodiment 1 of the invention.

As shown in FIG. 2, the image generation unit 6 of the processor 22 has a configuration in which a signal processing unit 17, a digital scan converter (DSC) 18, and an image processing unit 19 are connected in series. The signal processing unit 17 executes reception focus processing of giving a delay to each piece of element data compliant with a set sound speed based on a reception delay pattern selected according to a control signal from the apparatus controller 13 and performing addition (phasing addition). With the reception focus processing, a sound ray signal in which a focus of the ultrasound echo is narrowed is generated. The signal processing unit 17 performs correction of attenuation of the generated sound ray signal due to a propagation distance according to a depth of a reflection position of the ultrasonic wave, and then, executes envelope detection processing to generate a B mode image signal as tomographic image information regarding a tissue in the subject. The B mode image signal generated in this way is output to the DSC 18.

The DSC 18 raster-converts the B mode image signal into an image signal compliant with a normal television signal scanning system, that is, a B mode image. The image processing unit 19 executes various kinds of necessary image processing, such as brightness correction, gradation correction, sharpness correction, and color correction, on image data obtained in the DSC 18, and then, outputs the B mode image signal to the display controller 7, the measurement target recognition unit 9, and the measurement unit 10. Hereinafter, the B mode image is simply referred to as an ultrasound image.

The display controller 7 of the processor 22 executes predetermined processing on the ultrasound image generated by the image generation unit 6 and displays the ultrasound image on the display unit 8 under the control of the apparatus controller 13. Though describe below, the display controller 7 displays a measurement result calculated by the measurement unit 10 on the display unit 8.

The display unit 8 of the ultrasound diagnostic apparatus 1 has a display screen (not shown), and displays the ultrasound image generated by the image generation unit 6, the measurement result calculated by the measurement unit 10, and the like on the display screen under the control of the display controller 7. The display unit 8 includes, for example, a display device, such as a liquid crystal display (LCD) or an organic electroluminescence display (organic EL display).

The operating unit 15 of the ultrasound diagnostic apparatus 1 is provided for a user to perform an input operation, and includes a touch sensor disposed to be superimposed on the display unit 8. The touch sensor is disposed to be superimposed on the display screen of the display unit 8, and is provided for the user to perform an input operation through a touch operation to bring a finger of the user, a stylus pen, or the like into contact with or close to the display screen. Information input by the user through the touch sensor of the operating unit 15 is sent to the apparatus controller 13 and the measurement position designation reception unit 14.

The measurement position designation reception unit 14 of the processor 22 receives designation of a measurement position on the ultrasound image displayed on the display unit 8 from the user through the operating unit 15. Here, the measurement position is an approximate position of a measurement target included in the ultrasound image. For example, in a case where the user touches a position on the ultrasound image displayed on the display unit 8 to designate the measurement position, the measurement position designation reception unit 14 receives user's designation of the measurement position.

The measurement target recognition unit 9 of the processor 22 recognizes a measurement target included in the ultrasound image by performing image recognition on the ultrasound image in a recognition range decided based on the measurement position received by the measurement position designation reception unit 14. Here, the recognition range is a range on the ultrasound image in which the measurement target recognition unit 9 recognizes the measurement target, and is, for example, a range including the measurement position received by the measurement position designation reception unit 14 and having a determined size. The measurement target can include a part to be a target of measurement, such as an organ, or a lesion part, such as a tumor, a cyst, or bleeding.

For example, the measurement target recognition unit 9 can recognize the measurement target in the ultrasound image using machine learning, such as deep learning. In this case, for example, a neural network can be constructed by making the measurement target recognition unit 9 learn a large amount of typical pattern data for the measurement target as positive data in advance and learn a large amount of pattern data other than the typical pattern data for the measurement target as negative data in advance. The measurement target recognition unit 9 can recognize a measurement target by calculating a length or the like of a characteristic portion for patterns included in the ultrasound image and classifying the patterns into learned pattern data using a calculation result and the constructed neural network.

In this case, the measurement target recognition unit 9 can recognize the measurement target by providing likelihood for the learned pattern data to the patterns included in the ultrasound image and performing threshold value determination for the likelihood. Here, the likelihood is a value representing likelihood of a pattern included in the ultrasound image for a plurality of pieces of learned pattern data. For example, in a case of the likelihood of the pattern included in the ultrasound image is high with respect to pattern data of a gallbladder, there is a high probability that the pattern included in the ultrasound image is the gallbladder.

Here, as a method of machine learning, for example, a method described in Csurka et al.: Visual Categorization with Bags of Keypoints, Proc. of ECCV Workshop on Statistical Learning in Computer Vision, pp. 59-74 (2004) or the like can be used.

For example, the measurement target recognition unit 9 may recognize a measurement target by storing typical pattern data as a template in advance, calculating similarity to pattern data while searching an image with a template, and considering that a measurement target is present at a place where similarity is equal to or greater than a threshold value and becomes a maximum.

The measurement algorithm setting unit 12 of the processor 22 sets a measurement algorithm for the measurement target recognized by the measurement target recognition unit 9. The measurement algorithm setting unit 12 stores measurement algorithms corresponding to a plurality of parts or the like to be a measurement target as an association table in advance, and sets a measurement algorithm with reference to the association table in a case where the measurement target is determined.

Here, in general, there are different measurement rules for the measurement targets. The measurement rule is a rule regarding which portion is measured and how the portion is measured with respect to a specific measurement target. For example, in a case where the measurement target is a gallbladder, the measurement rule is that a line segment, which as two points on an inner wall of a gallbladder region included in the ultrasound image as end points, passes through the center of gravity of the gallbladder region, and has a maximum distance, is decided as a measurement line, and a length of the decided line segment is measured. Furthermore, for example, in a case where the measurement target is a kidney, the measurement rule determines that a length between two points having a maximum distance among two points on a boundary of a kidney region included in the ultrasound image is measured. The measurement algorithm defines calculation means for executing such a measurement rule, and is different for each measurement target.

Here, the algorithm defines calculation means for achieving the purpose, such as measurement. For example, the algorithm is implemented in the apparatus as a software program and is executed by a central processing unit (CPU). As the measurement algorithm set in the measurement algorithm setting unit 12, a known algorithm that is generally used can be used.

The measurement unit 10 of the processor 22 measures the measurement target recognized by the measurement target recognition unit 9 based on the measurement algorithm set by the measurement algorithm setting unit 12 and displays a measurement result on the display unit 8 through the display controller 7. Here, the measurement result that is displayed on the display unit 8 by the measurement unit 10 may include a name of the measurement target, a measurement line and a caliper used for measurement, and the like in addition to a measurement value of the measurement target.

The storage unit 16 of the ultrasound diagnostic apparatus 1 stores an operation program and the like of the ultrasound diagnostic apparatus 1, and a recording medium, such as a hard disc drive (HDD), a solid state drive (SSD), a flexible disc (FD), a magneto-optical disc (MO disc), a magnetic tape (MT), a random access memory (RAM), a compact disc (CD), a digital versatile disc (DVD), a secure digital card (SD card), or a universal serial bus memory (USB memory), a server, or the like can be used.

The processor 22 having the AD conversion unit 5, the image generation unit 6, the display controller 7, the measurement target recognition unit 9, the measurement unit 10, the measurement algorithm setting unit 12, the apparatus controller 13, and the measurement position designation reception unit 14 is configured of a central processing unit (CPU) and a control program causing the CPU to execute various kinds of processing. However, the processor 22 may be configured using a field programmable gate array (FPGA), a digital signal processor (DSP), an application specific integrated circuit (ASIC), a graphics processing unit (GPU), or other integrated circuits (ICs) or may be configured by combining the IC circuits.

The AD conversion unit 5, the image generation unit 6, the display controller 7, the measurement target recognition unit 9, the measurement unit 10, the measurement algorithm setting unit 12, the apparatus controller 13, and the measurement position designation reception unit 14 of the processor 22 may be configured to be partially or wholly integrated into one CPU or the like.

Figure 3:
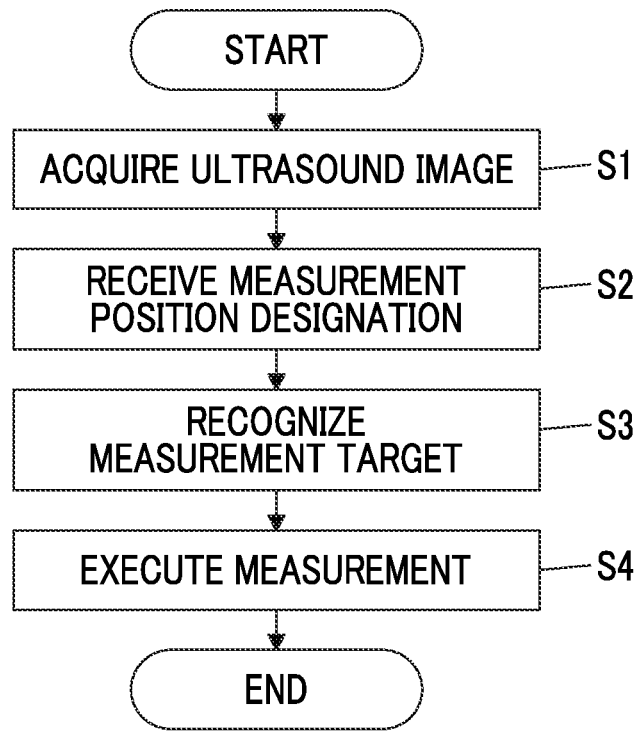
FIG. 3 is a flowchart showing the operation of the ultrasound diagnostic apparatus according to Embodiment 1 of the invention.

Next, the operation of the ultrasound diagnostic apparatus 1 of Embodiment 1 will be described referring to a flowchart shown in FIG. 3.

First, in Step S1, at least one ultrasound image is acquired by the ultrasound diagnostic apparatus 1, and the acquired one ultrasound image is displayed on the display unit 8. As the one ultrasound image displayed on the display unit 8, for example, an ultrasound image captured on the spot using the ultrasound probe 21 can be used. In this case, for example, in a state in which a plurality of ultrasound images are continuously captured by the ultrasound probe 21, and the ultrasound images are displayed sequentially on the display unit 8, the user performs an input operation through the operating unit 15, whereby one ultrasound image can be frozen and displayed on the display unit 8. As the one ultrasound image displayed on the display unit 8, an ultrasound image acquired from an external memory (not shown) may be used.

Figure 4:
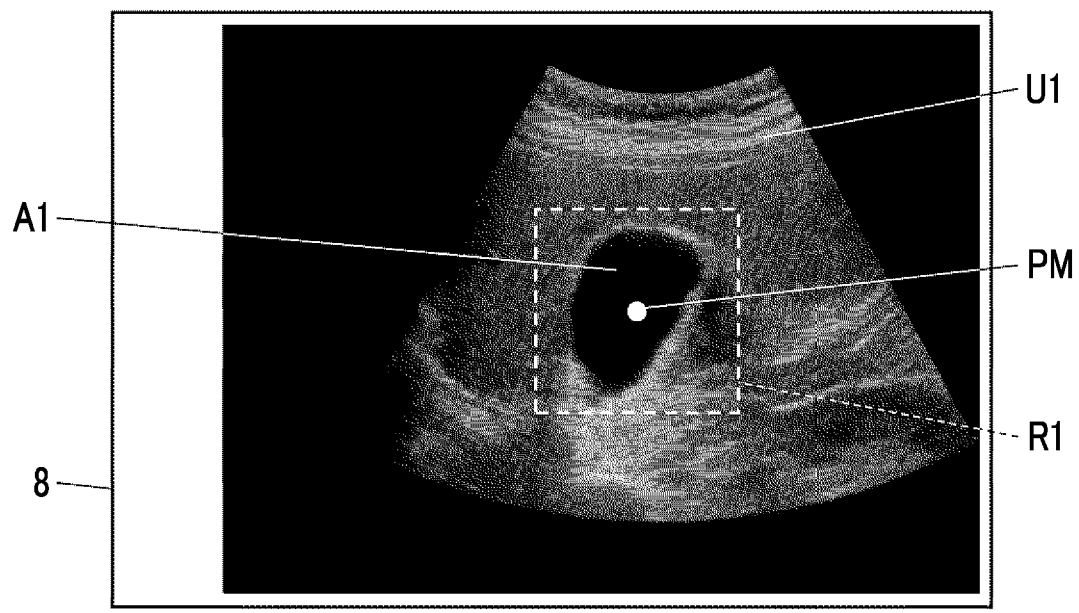
FIG. 4 is a diagram showing an example of a recognition range in Embodiment 1 of the invention.

Next, in Step S2, as shown in FIG. 4, a measurement position PM on an ultrasound image U1 displayed on the display unit 8 is touched and designated by the user, the measurement position designation reception unit 14 receives the user's designation of the measurement position PM. In this case, the user may designate a point positioned in a region representing a measurement target in the ultrasound image U1 or in the vicinity of the region as the measurement position PM. In an example shown in FIG. 4, a gallbladder A1 is included in the ultrasound image U1, the measurement position PM is designated on the gallbladder A1 in the ultrasound image U1. In this manner, in a case where the designation of the measurement position PM is received by the measurement position designation reception unit 14, subsequent Steps S3 and S4 are automatically executed sequentially by the ultrasound diagnostic apparatus 1.

In subsequent Step S3, the measurement target recognition unit 9 recognizes the measurement target in the ultrasound image U1 in a recognition range R1 including the measurement position PM designated by the user and having a determined size. For example, in the example shown in FIG. 4, the recognition range R1 is a square range in which the measurement position PM is disposed at the center, and includes the gallbladder A1. In this case, the measurement target recognition unit 9 recognizes the gallbladder A1 as the measurement target.

In a case where the measurement target is recognized in this manner, in Step S4, measurement of the measurement target is executed. Step S4 will be described in detail referring to a flowchart of FIG. 5.

Figure 5:
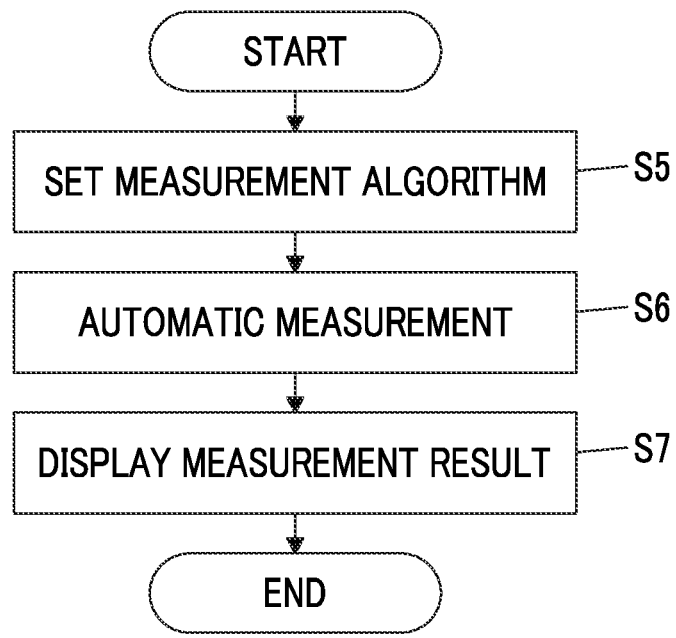
FIG. 5 is a flowchart showing an operation of measurement in Embodiment 1 of the invention.

As shown in FIG. 5, Step S4 includes three steps of Steps S5 to S7. First, in Step S5, the measurement algorithm setting unit 12 sets a measurement algorithm for the measurement target recognized in Step S3.

Figure 6:
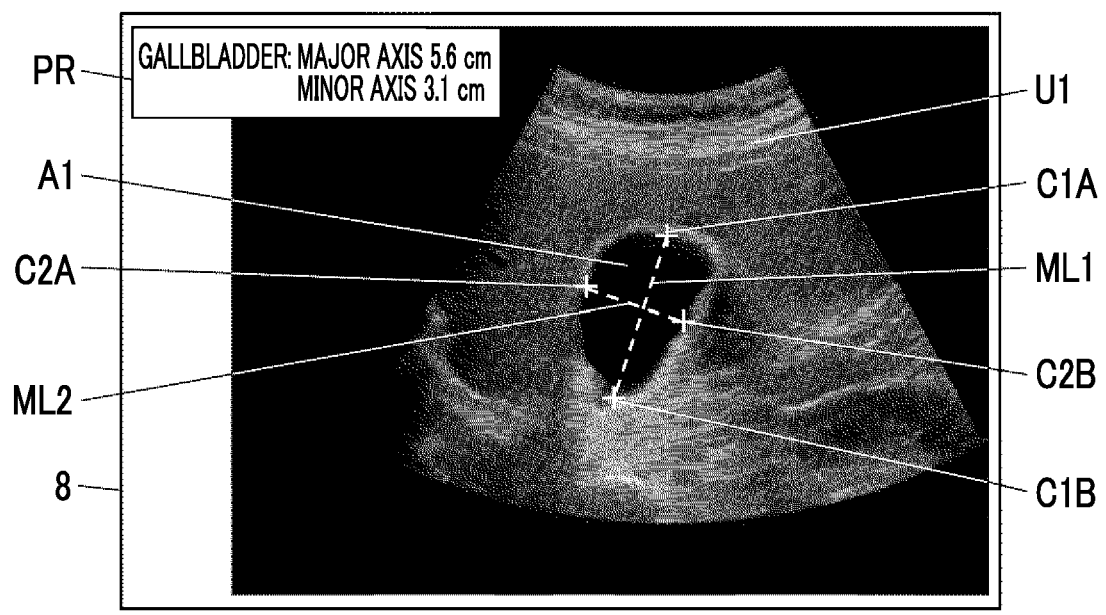
FIG. 6 is a diagram showing an example of a measurement result in Embodiment 1 of the invention.

For example, in a case where the measurement target is the gallbladder A1, as shown in FIG. 6, the measurement algorithm setting unit 12 sets a measurement algorithm that a line segment having a maximum distance with two points disposed on an inner wall of a region representing the gallbladder A1 in the ultrasound image U1 as end points is decided as a measurement line, and a length of the measurement line is measured. In the example shown in FIG. 6, a measurement line ML1 having calipers C1A and CB as end points and a measurement line ML2, which is perpendicular to the measurement line ML1 and has calipers C2A and C2B as end points, are set in two directions perpendicular to each other such that a distance between two points on the inner wall of the gallbladder A1 becomes a maximum.

In this way, the measurement algorithm setting unit 12 sets the measurement algorithm according to the measurement target recognized in Step S3. In this case, the measurement algorithm setting unit 12 may set a measurement algorithm for measuring an area other than the measurement algorithm for measuring the length or may set a measurement algorithm for measuring both of the length and the area according to the measurement target.

In subsequent Step S6, the measurement unit 10 executes automatic measurement of the measurement target based on the measurement algorithm set in Step S5. In a case where a measurement value of the measurement target is calculated by the automatic measurement, the measurement unit 10 displays a measurement result on the display unit 8 in Step S7. In this case, as shown in FIG. 6, the measurement unit 10 can display, as the measurement result, the measurement line ML1 having the calipers C1A and C1B as end points, the measurement line ML2 having the calipers C2A and C2B as end points, and a measurement result panel PR representing a name and a measurement value of the measurement target to be superimposed on the ultrasound image U1. The measurement result panel PR in FIG. 6 shows that a length of the measurement line ML1, that is, a length in a major axis direction of the gallbladder A1 is 5.6 cm and a length of the measurement line ML2, that is, a length in a minor axis direction of the gallbladder A1 is 3.1 cm.

In a case where the measurement result is displayed on the display unit 8 in this manner, the processing of Step S4 including Steps S5 to S7 is completed, and the operation of the ultrasound diagnostic apparatus 1 ends.

From the above, with the ultrasound diagnostic apparatus 1 of Embodiment 1, in a case where the measurement position PM that is an approximate position of the measurement target included in the ultrasound image U1 displayed on the display unit 8 is designated by the user, and the designation of the measurement position PM is received by the measurement position designation reception unit 14, a series of operations including the recognition of the measurement target in the recognition range R1, the setting of the measurement algorithm, and the measurement of the measurement target, and the display of the measurement result is automatically performed. Thus, it is possible to conveniently execute measurement.

In addition, with the ultrasound diagnostic apparatus 1 of Embodiment 1, the recognition of the measurement target is performed by the measurement target recognition unit 9 only in the recognition range R1 including the measurement position PM received by the measurement position designation reception unit 14 and having the determined size. Thus, it is possible to reduce a calculation load required for the recognition of the measurement target, making it possible to promptly recognize the measurement target.

In Embodiment 1, although an example where the measurement target is included in the recognition range R1 has been described, a measurement target may not be included in the recognition range R1. In this case, in Step S3, the measurement target recognition unit 9 cannot recognize a measurement target in the recognition range R1. Thus, for example, the operation of the ultrasound diagnostic apparatus 1 can end without executing the automatic measurement of Step S4. In this case, a message to the effect that a measurement target cannot be found can be displayed on the display unit 8.

Although the measurement algorithm setting unit 12 automatically sets the measurement algorithm according to the measurement target recognized in Step S3, the measurement algorithm to be set can be set to a measurement algorithm conforming to a user's preference or the like in advance. For example, as shown in FIG. 6, a first measurement algorithm for measuring both of the length in the major axis direction, that is, the length of the measurement line ML1 and the length in the minor axis direction, that is, the length of the measurement line ML2, a second measurement algorithm for measuring only the length of the measurement line ML1 in the major axis direction, and a third measurement algorithm for measuring only the length of the measurement line ML2 in the minor axis direction are prepared for the gallbladder A1, and the user is prompted to select one of the three measurement algorithms in advance through the operating unit 15. Thereby, it is possible to set the measurement algorithm for the gallbladder A1 to the measurement algorithm conforming to the user's preference.

In displaying the measurement result on the display unit 8, in a case where a plurality of measurement values are calculated, the measurement unit 10 can display a plurality of measurement values, names of a plurality of corresponding measurement targets, a plurality of corresponding measurement lines, a plurality of corresponding calipers, and the like in different aspects for the respective measurement values. For example, the measurement unit 10 can display each measurement value on the display unit 8 by making at least one of a color, a thickness, a kind of a line, such as a solid line or a broken line, or transmittance of an item related to each measurement value different.

In Embodiment 1, although the recognition range R1 having a square shape is illustrated, the shape of the recognition range R1 is not limited to the square shape. For example, the recognition range R1 has a rectangular shape, a circular shape, or a polygonal shape, and can have any shape as long as the recognition range is a closed range.

Embodiment 2

In Embodiment 1, in a case where the ultrasound image U1 displayed on the display unit 8 is touched by the user and the measurement position PM is designated, the designation of the measurement position PM is received by the measurement position designation reception unit 14, a series of operations including the decision of the recognition range R1, the recognition of the measurement target, the setting of the measurement algorithm, the measurement of the measurement target, and the display of the measurement result is automatically performed. In contrast, the series of operations may be executed with an instruction from the user through the operating unit 15 as a trigger.

Figure 7:
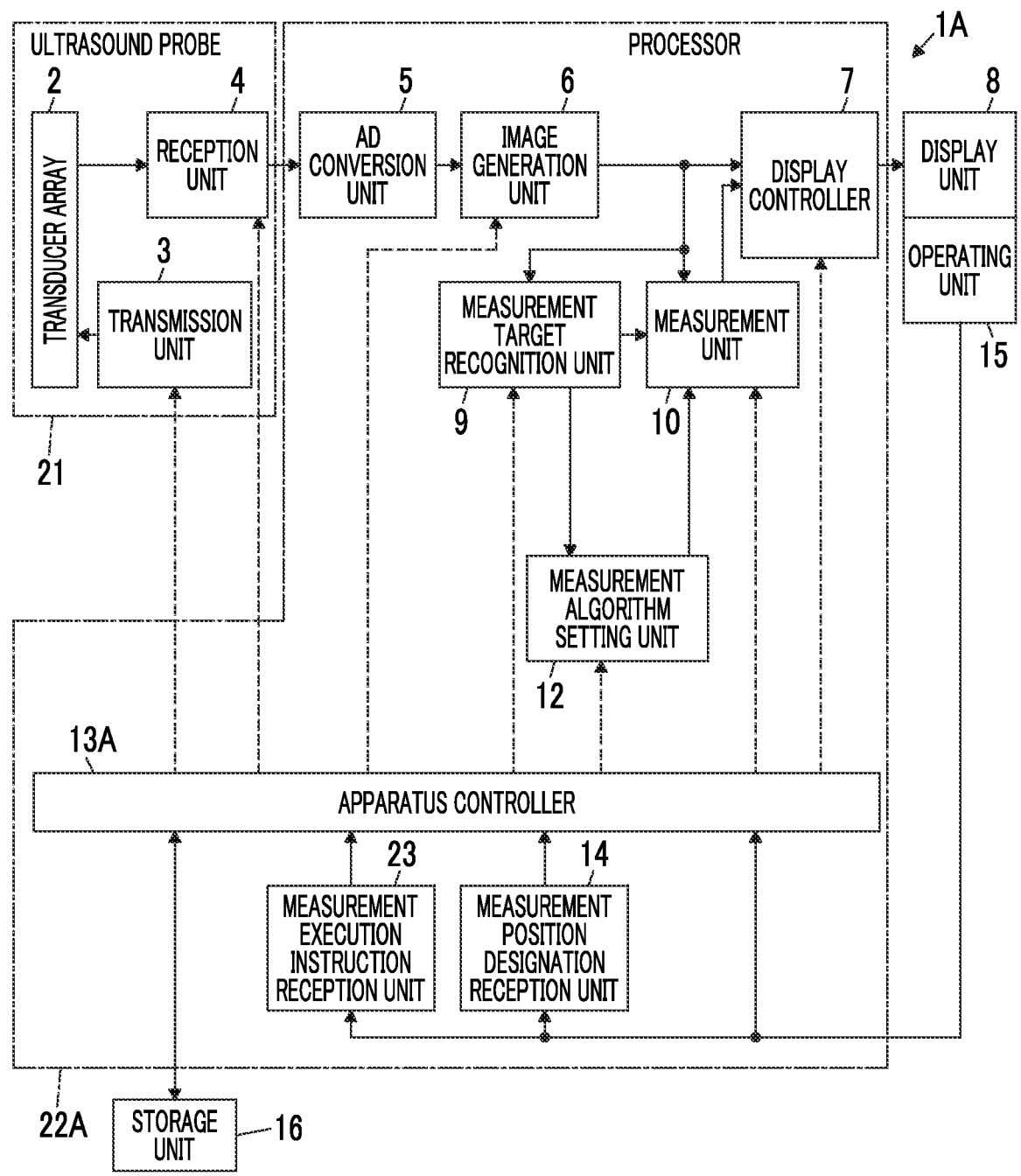
FIG. 7 is a block diagram showing the configuration of an ultrasound diagnostic apparatus according to Embodiment 2 of the invention.

FIG. 7 shows the configuration of an ultrasound diagnostic apparatus 1A according to Embodiment 2. The ultrasound diagnostic apparatus 1A of Embodiment 2 comprises an apparatus controller 13A instead of the apparatus controller 13 in the ultrasound diagnostic apparatus 1 of Embodiment 1 shown in FIG. 1, and further comprises a measurement execution instruction reception unit 23.

In the ultrasound diagnostic apparatus 1A of Embodiment 2, the apparatus controller 13A is connected to the transmission unit 3, the reception unit 4, the image generation unit 6, the display controller 7, the measurement target recognition unit 9, the measurement unit 10, the measurement algorithm setting unit 12, the measurement position designation reception unit 14, the operating unit 15, and the storage unit 16. The measurement execution instruction reception unit 23 is connected to the apparatus controller 13A, and the measurement execution instruction reception unit 23 is further connected to the operating unit 15.

The AD conversion unit 5, the image generation unit 6, the display controller 7, the measurement target recognition unit 9, the measurement unit 10, the measurement algorithm setting unit 12, the apparatus controller 13A, the measurement position designation reception unit 14, and the measurement execution instruction reception unit 23 configure a processor 22A.

The measurement execution instruction reception unit 23 of the processor 22A receives a measurement execution instruction input from the user through the operating unit 15 for the measurement target recognized by the measurement target recognition unit 9. Information representing the measurement execution instruction received by the measurement execution instruction reception unit 23 is sent to the apparatus controller 13A, and a series of operations relating to measurement is started based on information representing the measurement execution instruction.

Figure 8:
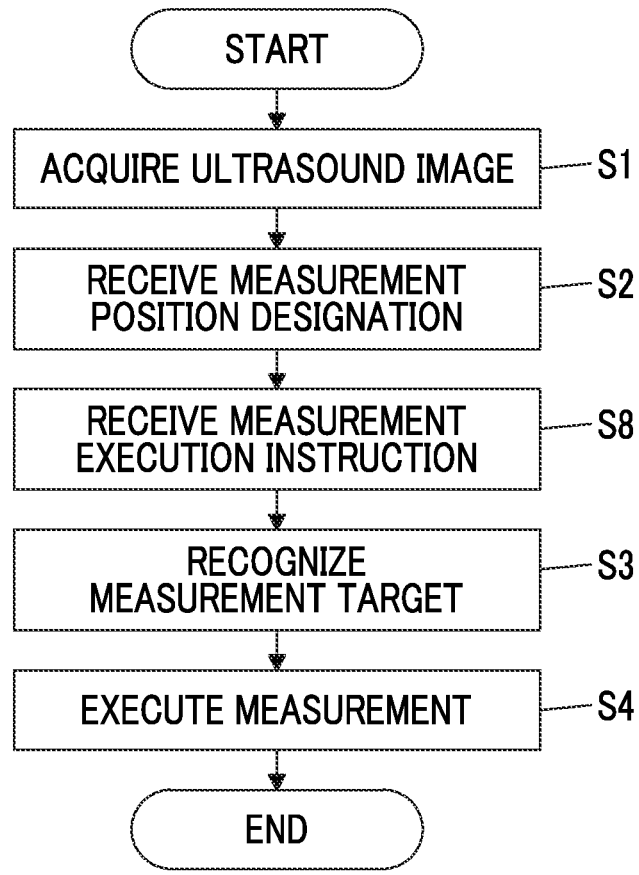
FIG. 8 is a flowchart showing the operation of the ultrasound diagnostic apparatus according to Embodiment 2 of the invention.

Next, the operation of the ultrasound diagnostic apparatus 1A of Embodiment 2 will be described referring to a flowchart shown in FIG. 8. The flowchart shown in FIG. 8 provides Step S8 between Steps S2 and S3 in the flowchart of Embodiment 1 shown in FIG. 3.

First, in Step S1, one ultrasound image U1 is acquired, and the acquired ultrasound image U1 is displayed on the display unit 8.

In Step S2, in a case where the user touches the ultrasound image U1 displayed on the display unit 8 to designate the measurement position PM, the measurement position designation reception unit 14 receives the user's designation of the measurement position PM.

Figure 9:
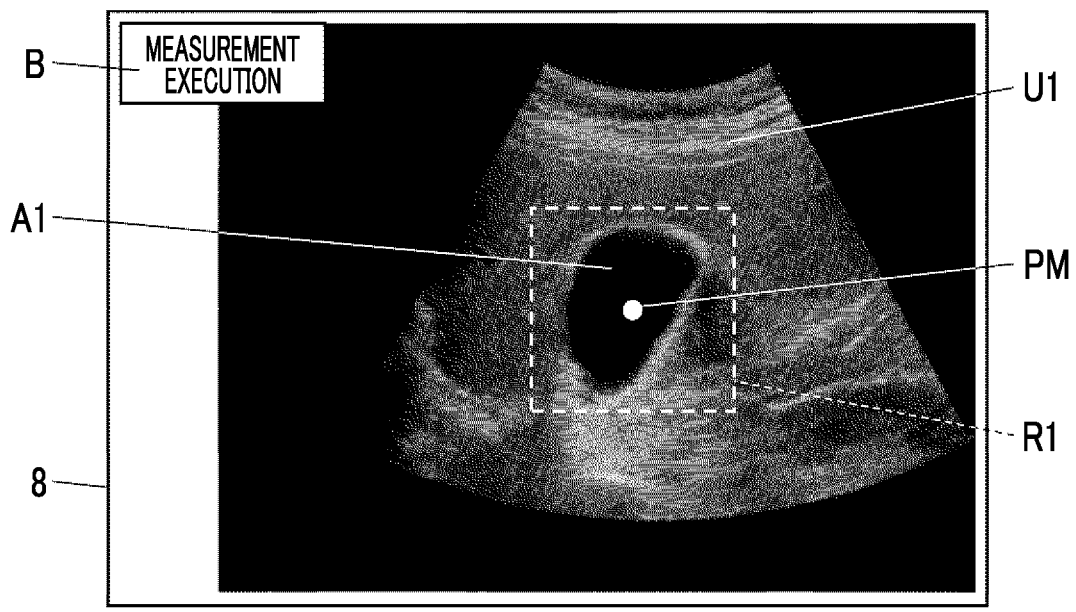
FIG. 9 is a diagram showing a measurement execution button in Embodiment 2 of the invention.

In subsequent Step S8, for example, as shown in FIG. 9, the measurement execution instruction reception unit 23 displays a measurement execution button B for the measurement execution instruction on the display unit 8, and the user touches the measurement execution button B through the operating unit 15, whereby the measurement execution instruction of the user is issued. The measurement execution instruction reception unit 23 receives the measurement execution instruction issued by the user in this manner and sends information representing the measurement execution instruction to the apparatus controller 13A.

Next, in Step S3, in a case where information representing the measurement execution instruction is received from the apparatus controller 13A, the measurement target recognition unit 9 recognizes a measurement target included in a recognition range R1 shown in FIG. 9. Here, in the example shown in FIG. 9, the recognition range R1 is a square range in which the measurement position PM is disposed at the center and which has a determined size.

In subsequent Step S4, automatic measurement for the measurement target recognized in Step S3 is executed, and the operation of the ultrasound diagnostic apparatus 1A ends.

From the above, with the ultrasound diagnostic apparatus 1A of Embodiment 2, a series of operations including the recognition of the measurement target in the recognition range R1, the setting of the measurement algorithm, the measurement of the measurement target, and the display of the measurement result is automatically performed with the reception of the measurement execution instruction from the user through the operating unit 15 by the measurement execution instruction reception unit 23 as a trigger. Thus, for example, even though the user designates a position away from the measurement target as a measurement position, the measurement position can be re-designated before the series of operates is started.

Step S8 of receiving the measurement execution instruction may be provided immediately after Step S3 of recognizing the measurement target, instead of being provided immediately after Step S2 of receiving the designation of the measurement position. In this case, in Step S8, for example, the measurement execution button B shown in FIG. 9 can be displayed on the display unit 8, and the name of the measurement target recognized in Step S3 can be displayed. With this, the user can issue the measurement execution instruction after ascertaining the measurement target recognized by the measurement target recognition unit 9.

Embodiment 3

In Embodiment 1 and Embodiment 2, although the recognition and the measurement of one measurement target included in the ultrasound image U are performed, recognition and measurement of a plurality of measurement targets may be performed.

Figure 10:
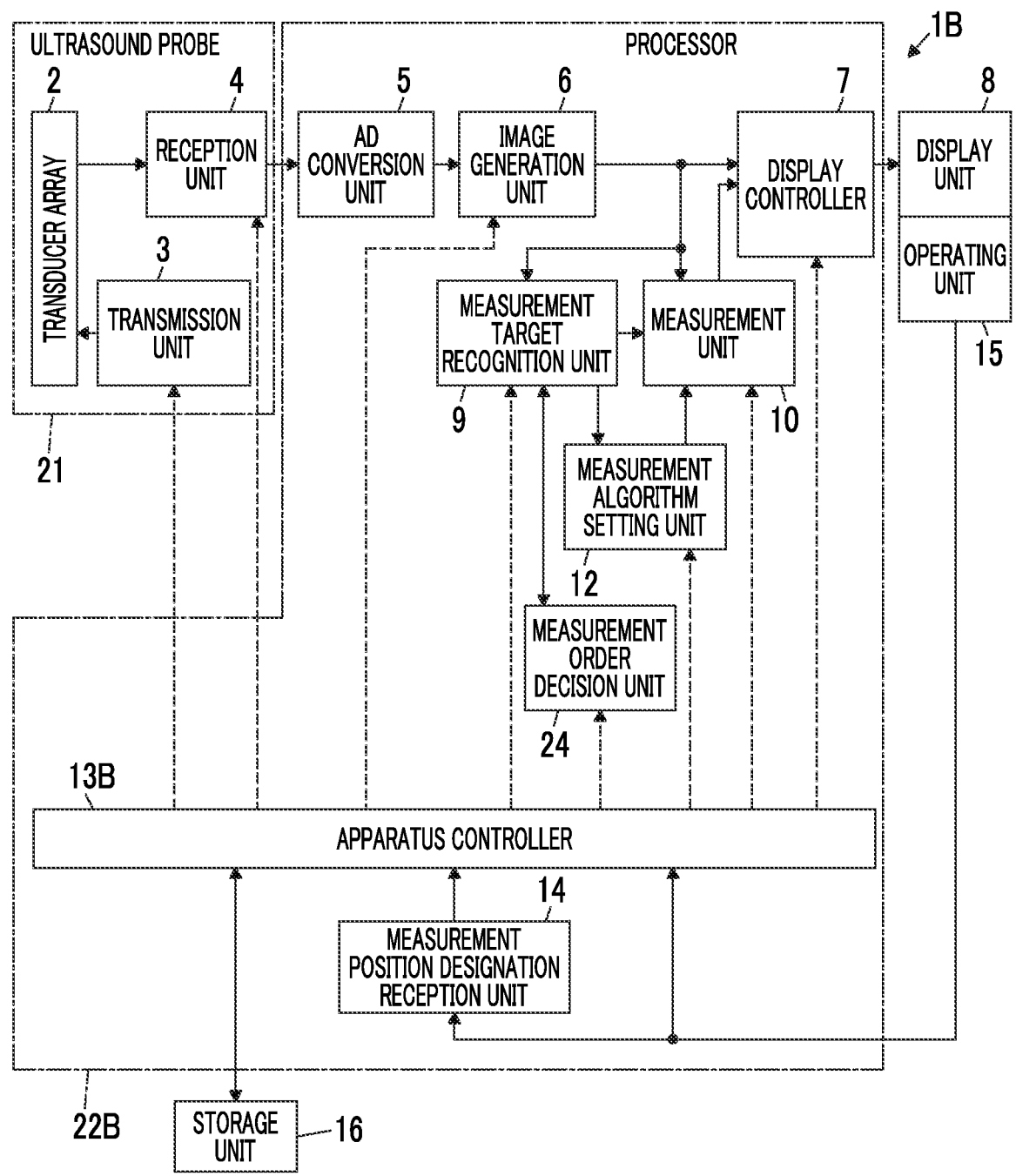
FIG. 10 is a block diagram showing the configuration of an ultrasound diagnostic apparatus according to Embodiment 3 of the invention.

FIG. 10 shows the configuration of an ultrasound diagnostic apparatus 1B according to Embodiment 3. The ultrasound diagnostic apparatus 1B of Embodiment 3 comprises an apparatus controller 13B instead of the apparatus controller 13 in the ultrasound diagnostic apparatus 1 of Embodiment 1 shown in FIG. 1, and further comprises a measurement order decision unit 24.

In the ultrasound diagnostic apparatus 1B of Embodiment 3, the measurement order decision unit 24 is connected to the measurement target recognition unit 9. Here, the measurement target recognition unit 9 and the measurement order decision unit 24 are connected so as to transmit information in two directions. The apparatus controller 13B is connected to the transmission unit 3, the reception unit 4, the image generation unit 6, the display controller 7, the measurement target recognition unit 9, the measurement unit 10, the measurement algorithm setting unit 12, the measurement position designation reception unit 14, the operating unit 15, and the storage unit 16.

The AD conversion unit 5, the image generation unit 6, the display controller 7, the measurement target recognition unit 9, the measurement unit 10, the measurement algorithm setting unit 12, the apparatus controller 13B, the measurement position designation reception unit 14, and the measurement order decision unit 24 configure a processor 22B.

In a case where a plurality of measurement targets are recognized in the recognition range by the measurement target recognition unit 9, the measurement order decision unit 24 of the processor 22B decides a measurement order of a plurality of measurement targets. The measurement order decision unit 24 sends the decided measurement order to the measurement unit 10 through the measurement target recognition unit 9.

The measurement unit 10 measures a plurality of measurement targets in compliance with the measurement order decided by the measurement order decision unit 24 under the control of the apparatus controller 13B.

Figure 11:
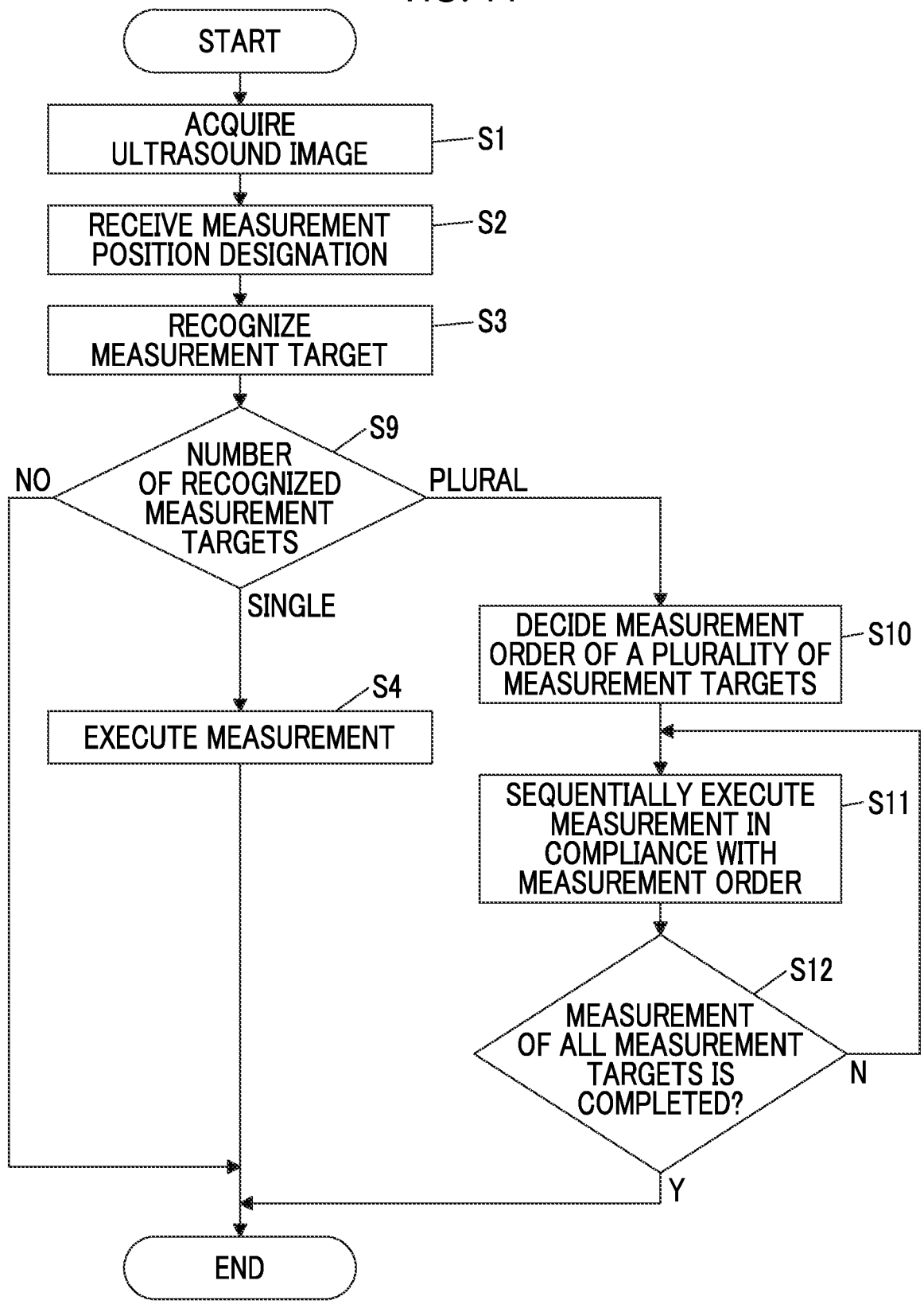
FIG. 11 is a flowchart showing the operation of the ultrasound diagnostic apparatus according to Embodiment 3 of the invention.

Next, the operation of the ultrasound diagnostic apparatus 1B of Embodiment 3 will be described referring to a flowchart shown in FIG. 11. Steps S1 to S4 in the flowchart of FIG. 11 are the same as Steps S1 to S4 in the flowchart shown in FIG. 3, respectively.

Figure 12:
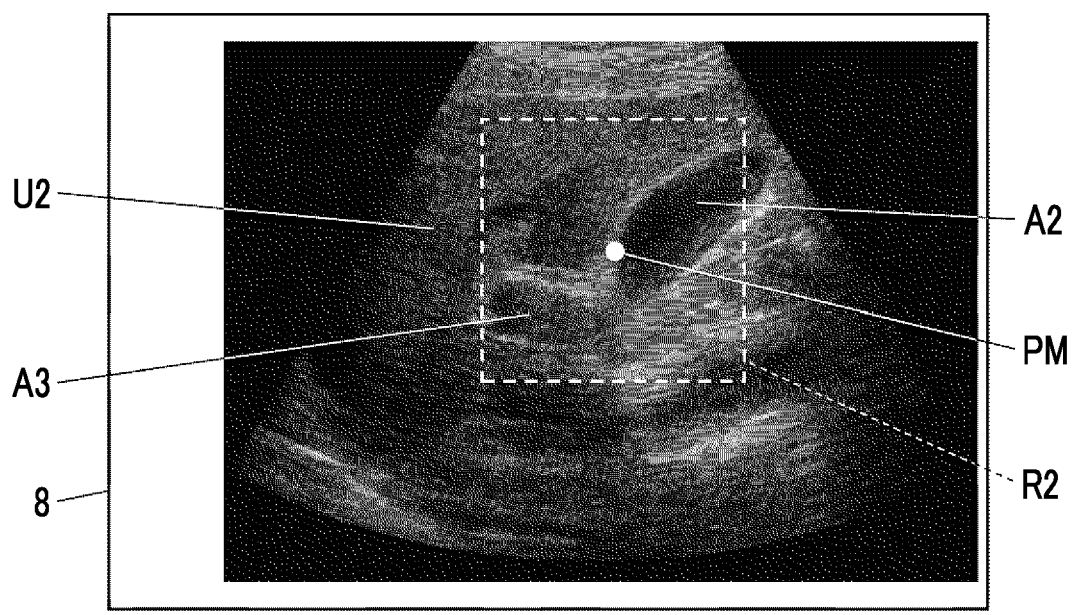
FIG. 12 is a diagram showing an example of a recognition range in Embodiment 3 of the invention.

In Step S1, one ultrasound image U2 is acquired, and as shown in FIG. 12, an acquired ultrasound image U2 is displayed on the display unit 8.

In Step S2, in a case where the user touches the ultrasound image U2 displayed on the display unit 8 to designate the measurement position PM, the measurement position designation reception unit 14 receives the user's designation of the measurement position PM.

In subsequent Step S3, the measurement target recognition unit 9 recognizes measurement targets included in a recognition range R2 shown in FIG. 12. Here, in the example shown in FIG. 12, the recognition range R2 is a square range in which the measurement position PM is disposed at the center and which has a determined size, and two measurement targets of a gallbladder A2 and a portal vein A3 are included in the recognition range R2. In this case, the measurement target recognition unit 9 can recognize the two measurement targets of the gallbladder A2 and the portal vein A3 included in the recognition range R2.

In subsequent Step S9, the measurement target recognition unit 9 determines the number of measurement targets recognized in Step S3. In a case where the number of measurement targets recognized in Step S3 is one, the process progresses to Step S4, automatic measurement is executed for one measurement target, and the operation of the ultrasound diagnostic apparatus 1B ends.

In a case where the number of measurement targets recognized in Step S3 is plural, the process progresses to Step S10, and the measurement order of a plurality of measurement targets is decided by the measurement order decision unit 24. In this case, for example, the measurement order decision unit 24 decides the measurement order of a plurality of measurement targets such that the closer the measurement target to the measurement position PM designated by the user on the ultrasound image U2, the earlier the measurement order. For example, in the example shown in FIG. 12, since the gallbladder A2 between the two recognized measurement targets is closer to the measurement position PM than the portal vein A3, the measurement order decision unit 24 can decide the measurement order such that automatic measurement is executed in the order of the gallbladder A2 and the portal vein A3.

In subsequent Step S11, automatic measurement is first executed for the measurement target having the earliest measurement order in compliance with the measurement order decided in Step S10. The automatic measurement executed in Step S1 is the same as the automatic measurement executed in Step S4. In a case where the automatic measurement of the first measurement target is executed in this manner, in Step S12, determination is made whether or not automatic measurement is completed for all measurement targets among a plurality of measurement targets recognized in Step S3. In a case where the automatic measurement is not completed for all measurement targets, the process returns to Step S11, and the automatic measurement of the measurement target having the next measurement order is executed. Here, the measurement results of the respective measurement targets can be displayed, for example, simultaneously on the display unit 8.

In this manner, until the automatic measurement is completed for all measurement targets, Steps S11 and S12 are repeated sequentially, and in a case where the automatic measurement is completed for all measurement targets, the operation of the ultrasound diagnostic apparatus 1 ends.

For example, in a case where no measurement target is included in the recognition range R2, or the like, and determination is made in Step S9 that there is no measurement target recognized in Step S3, automatic measurement is not executed, and the operation of the ultrasound diagnostic apparatus 1B ends. In this case, a message to the effect that a measurement target cannot be found may be displayed on the display unit 8.

From the above, with the ultrasound diagnostic apparatus 1B of Embodiment 3, in a case where a plurality of measurement targets included in the recognition range R2 are recognized, the measurement order of a plurality of measurement targets is decided, and the automatic measurement is executed sequentially in compliance with the decided measurement order. Thus, even though a plurality of measurement targets are included in the recognition range, as in Embodiment 1, it is possible to conveniently execute measurement.

In Embodiment 3, although the measurement order decision unit 24 decides the measurement order for all measurement targets recognized by the measurement target recognition unit 9, a measurement order may be decided for a part of measurement targets among a plurality of measurement targets recognized by the measurement target recognition unit 9. For example, the measurement order decision unit 24 can decide a measurement order only for a determined number of measurement targets, such as two or three, among a plurality of measurement targets recognized by the measurement target recognition unit 9 such that the closer the measurement target to the measurement position, the earlier the measurement order. In this case, the ultrasound diagnostic apparatus 1B can execute automatic measurement only for the measurement targets having the decided measurement order. In this way, in a case where a plurality of measurement targets are recognized by the measurement target recognition unit 9, the measurement order is decided only for a part of measurement targets, and the automatic measurement is executed in compliance with the decided measurement order. Thereby, it is possible to execute automatic measurement only for a highly useful measurement target positioned in the vicinity of the measurement position designated by the user.

In a case where a plurality of measurement targets are recognized by the measurement target recognition unit 9, and the measurement of a plurality of measurement targets is executed by the measurement unit 10, the measurement unit 10 can display a plurality of obtained measurement results on the display unit 8 in various aspects.

Figure 13:
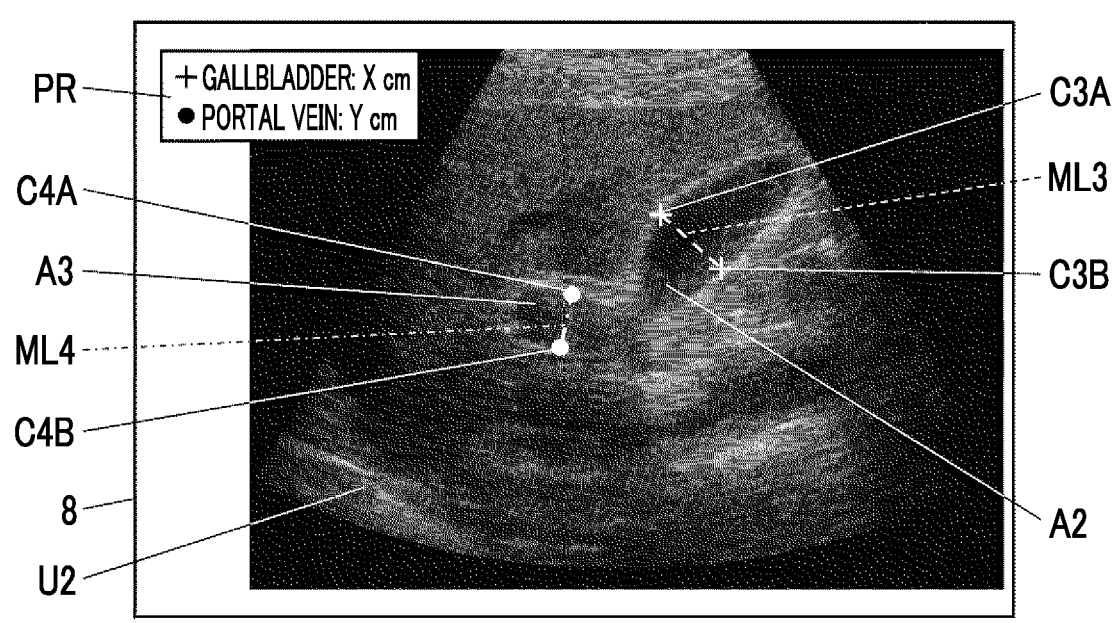
FIG. 13 is a diagram showing an example of a measurement result in a modification example of Embodiment 3 of the invention.

For example, as shown in FIG. 13, in a case where a gallbladder A2 and a portal vein A3 are recognized as measurement targets by the measurement target recognition unit 9, the measurement unit 10 can make shapes of a pair of calipers C3A and C3B for measuring a length of the gallbladder A2 different from shapes of a pair of calipers C4A and C4B for measuring a length of the portal vein A3. In this case, as shown in FIG. 13, the measurement unit 10 can display a mark corresponding to a pair of calipers C3A and C3B used for the measurement of the gallbladder A2 and a mark corresponding to a pair of calipers C4A and C4B used for the measurement of the portal vein A3 in parallel with the names of the measurement targets in a measurement result panel PR. With this, the user can easily associate and ascertain the respective measurement targets and the measurement results.

For example, though not shown, the measurement unit 10 may display the names and the measurement values corresponding to a plurality of measurement targets on the display unit 8 and may display a leading line connecting each measurement target and the corresponding name and measurement value.

For example, though not shown, the measurement unit 10 may display the name and the measurement value corresponding to each measurement target in the vicinity of a plurality of measurement targets on the ultrasound image U2.

For example, the measurement unit 10 may display at least one of the measurement lines or the calipers displayed to be superimposed on a plurality of measurement targets and the corresponding names and measurement values in different colors by measurement target.

The measurement results are displayed using the above-described aspects, whereby the user can easily associate and ascertain each measurement target and the measurement result. Various aspects of displaying the measurement results can be used in appropriate combinations.

Embodiment 4

In Embodiment 3, in a case where a plurality of measurement targets are included in the recognition range R2, the measurement is automatically executed for a plurality of measurement targets. In contrast, the user may be prompted to select a measurement target that is actually measured among a plurality of measurement targets.

Figure 14:
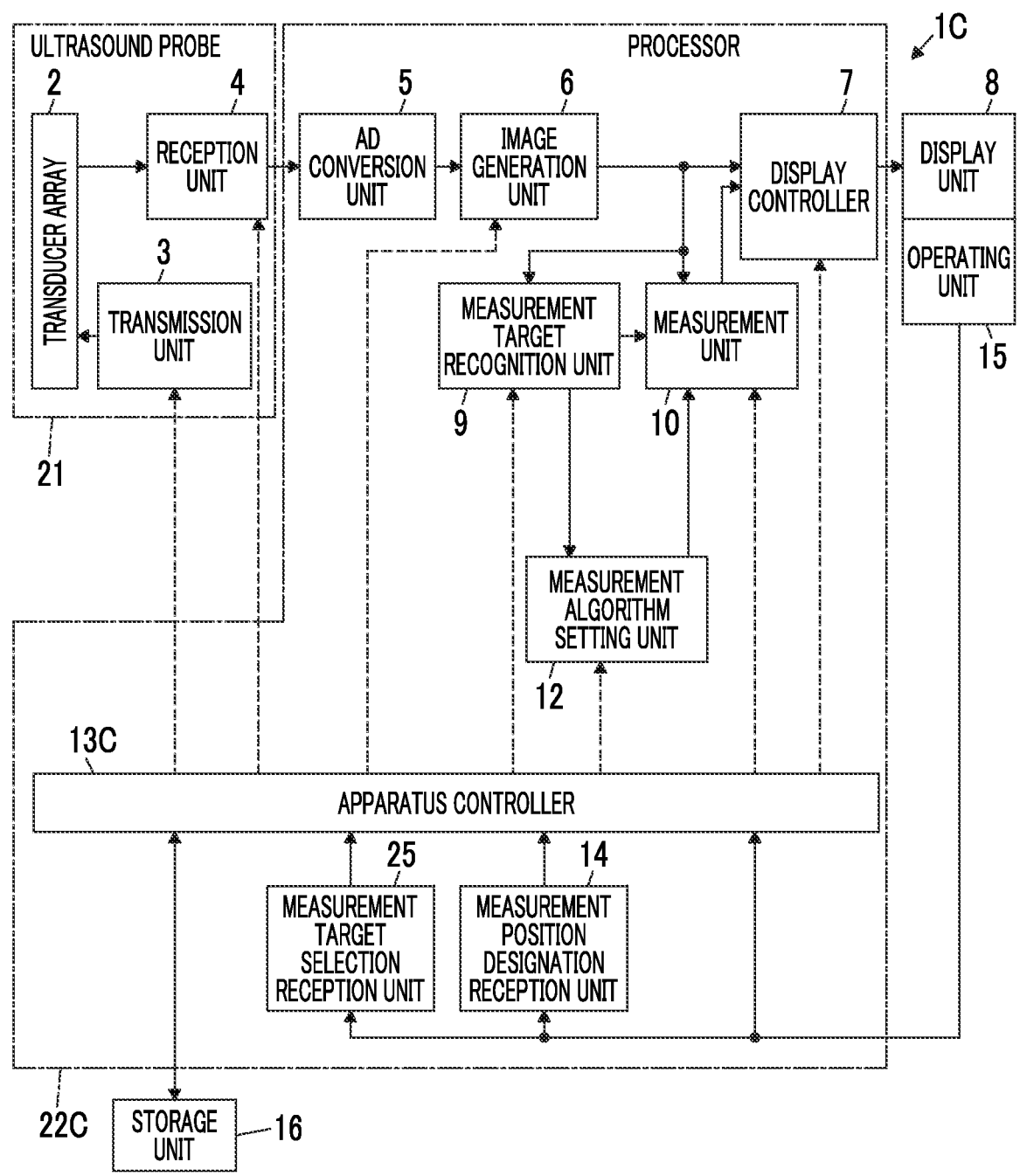
FIG. 14 is a block diagram showing the configuration of an ultrasound diagnostic apparatus according to Embodiment 4 of the invention.

FIG. 14 shows the configuration of an ultrasound diagnostic apparatus 1C according to Embodiment 4. The ultrasound diagnostic apparatus 1C of Embodiment 5 comprises an apparatus controller 13C instead of the apparatus controller 13 in the ultrasound diagnostic apparatus 1 of Embodiment 1 shown in FIG. 1, and further comprises a measurement target selection reception unit 25.

In the ultrasound diagnostic apparatus 1C of Embodiment 5, the apparatus controller 13C is connected to the transmission unit 3, the reception unit 4, the image generation unit 6, the display controller 7, the measurement target recognition unit 9, the measurement unit 10, the measurement algorithm setting unit 12, the measurement position designation reception unit 14, the operating unit 15, and the storage unit 16. The measurement target selection reception unit 25 is connected to the apparatus controller 13C, and the measurement target selection reception unit 25 is connected to the operating unit 15.

The AD conversion unit 5, the image generation unit 6, the display controller 7, the measurement target recognition unit 9, the measurement unit 10, the measurement algorithm setting unit 12, the apparatus controller 13C, the measurement position designation reception unit 14, and the measurement target selection reception unit 25 configure a processor 22C.

The measurement target selection reception unit 25 of the processor 22C receives selection of one measurement target among a plurality of measurement targets from the user through the operating unit 15 in a case where a plurality of measurement targets are recognized by the measurement target recognition unit 9 in a recognition range including the measurement position PM received by the measurement position designation reception unit 14 and having a determined size. For one measurement target of which the selection is received by the measurement target selection reception unit 25, automatic measurement is executed under the control of the apparatus controller 13C.

Figure 15:
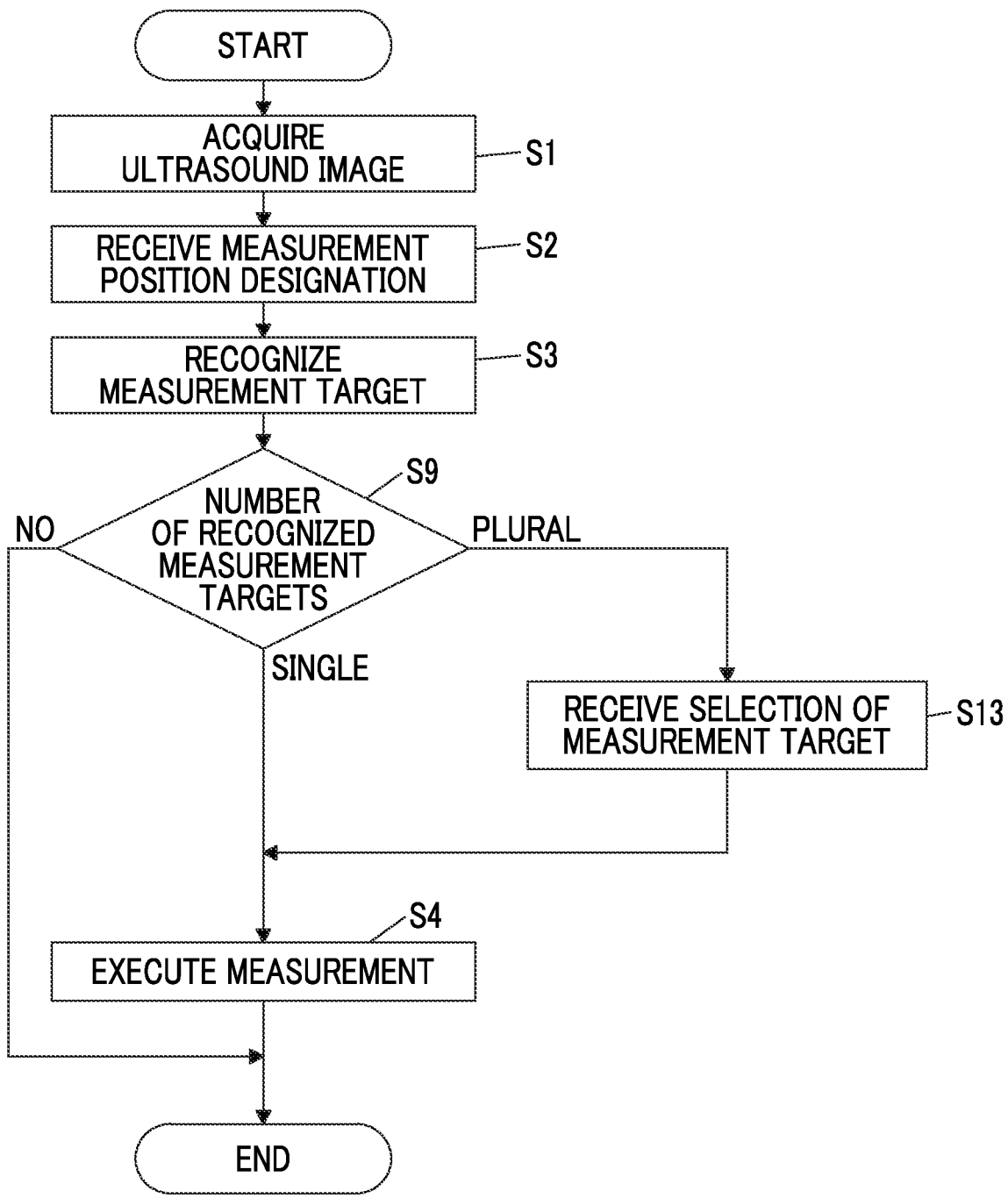
FIG. 15 is a flowchart showing the operation of the ultrasound diagnostic apparatus according to Embodiment 4 of the invention.

Next, the operation of the ultrasound diagnostic apparatus 1C of Embodiment 4 will be described referring to a flowchart of FIG. 15. The flowchart shown in FIG. 15 provides Step S13 instead of Steps S10 to S12 in the flowchart of Embodiment 3 shown in FIG. 11.

Figure 16:
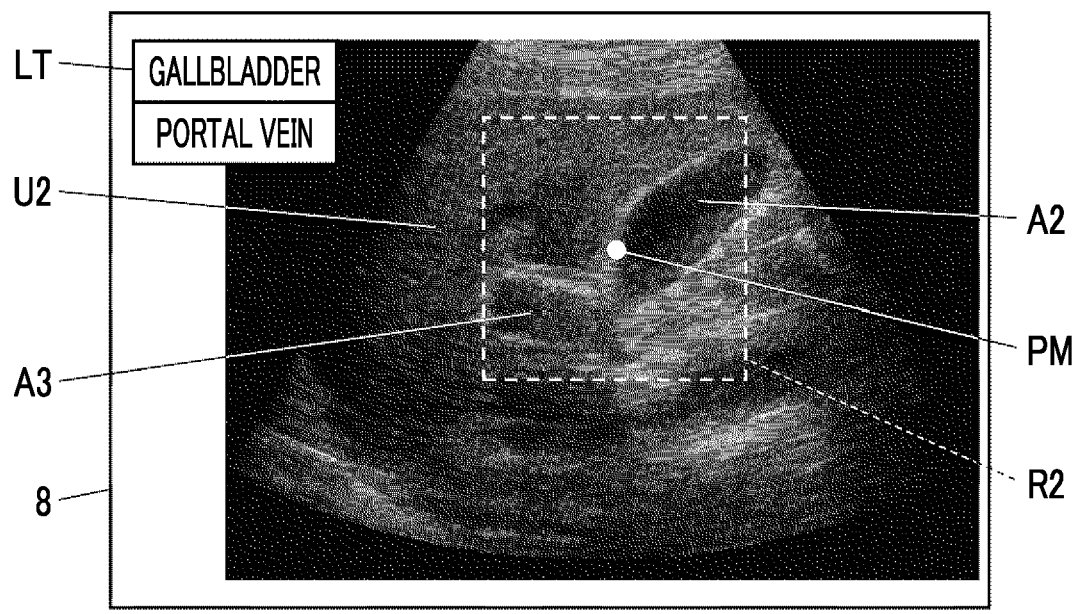
FIG. 16 is a diagram showing an example of a measurement target list in Embodiment 4 of the invention.

First, in Step S1, one ultrasound image U2 shown in FIG. 16 is acquired, and the acquired ultrasound image U2 is displayed on the display unit 8.

In Step S2, in a case where the user touches the ultrasound image U2 displayed on the display unit 8 to designate the measurement position PM, the measurement position designation reception unit 14 receives the user's designation of the measurement position PM.

Next, in Step S3, the measurement target recognition unit 9 recognizes measurement targets included in a recognition range R2 shown in FIG. 16. In the example shown in FIG. 16, two measurement targets of a gallbladder A2 and a portal vein A3 are included in the recognition range R2, and the measurement target recognition unit 9 recognizes the gallbladder A2 and the portal vein A3 included in the recognition range R2.

In subsequent Step S9, the measurement target recognition unit 9 determines the number of measurement targets recognized in Step S3. In a case where the number of measurement targets recognized in Step S3 is one, the process progresses to Step S4, automatic measurement is executed for one measurement target, and the operation of the ultrasound diagnostic apparatus 1C ends.

In a case where the number of measurement targets recognized in Step S3 is plural, the process progresses to Step S13, selection of one of a plurality of measurement targets is received from the user through the operating unit 15 by the measurement target selection reception unit 25. In this case, for example, as shown in FIG. 16, the names of a plurality of measurement targets recognized in Step S3, such as "gallbladder" and "portal vein", can be displayed in a list, and a measurement target list LT on which a name of a measurement target is selectable through the operating unit 15 can be displayed on the display unit 8. For example, when "gallbladder" between "gallbladder" and "portal vein" displayed on the measurement target list LT is touched by the user, the measurement target selection reception unit 25 receives the selection of the gallbladder A2 as a measurement target.

In subsequent Step S4, automatic measurement is executed for the measurement target which is selected by the user in Step S13 and of which the selection is received by the measurement target selection reception unit 25. In this case, in a case where the automatic measurement of one measurement target selected in Step S13 is completed, the operation of the ultrasound diagnostic apparatus 1C ends.

For example, in a case where no measurement target is included in the recognition range R2, or the like, and determination is made in Step S9 that there is no measurement target recognized in Step S3, automatic measurement is not executed, and the operation of the ultrasound diagnostic apparatus 1C ends. In this case, a message to the effect that a measurement target cannot be found may be displayed on the display unit 8.

From the above, with the ultrasound diagnostic apparatus 1C of Embodiment 4, in a case where a plurality of measurement targets are recognized by the measurement target recognition unit 9, one of a plurality of measurement targets is selected by the user through the operating unit 15, and the automatic measurement is executed for the selected measurement target. Thus, even though a plurality of measurement targets are recognized, it is possible to execute automatic measurement only for a measurement target intended by the user.

In Embodiment 4, although the measurement target list LT is displayed on the display unit 8, and the user is prompted to select one of the names of a plurality of measurement targets on the measurement target list LT through the operating unit 15, a method of selecting a measurement target is not limited thereto.

Figure 17:
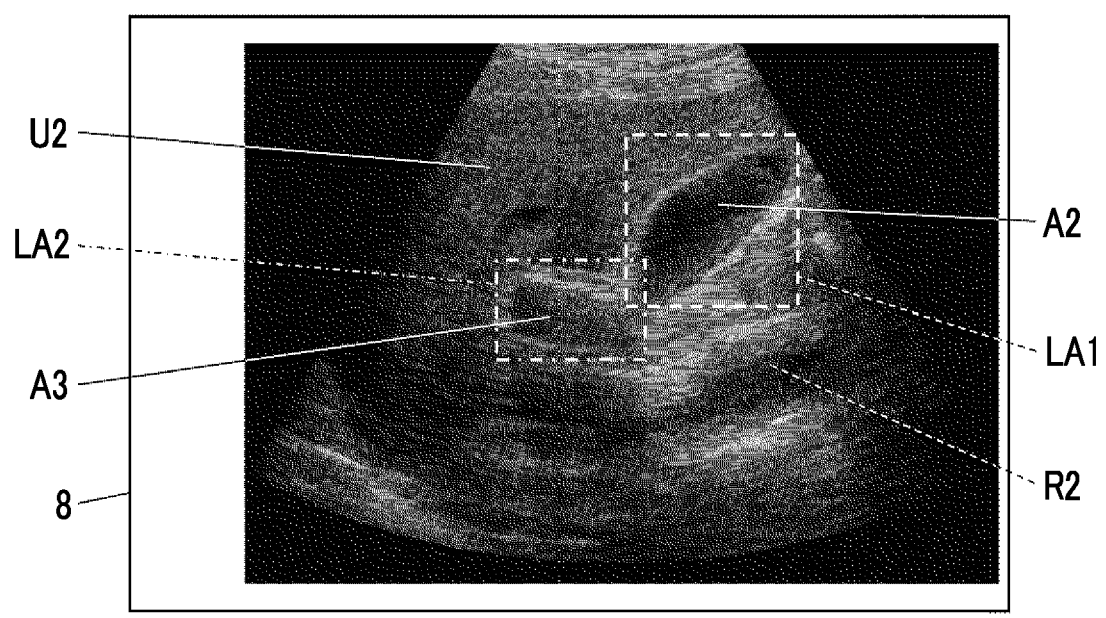
FIG. 17 is a diagram showing an example of a target region line in a modification example of Embodiment 4 of the invention.

For example, as shown in FIG. 17, a target region line LA1 that represents a closed region only including the gallbladder A2 as a measurement target and a target region line LA2 that represents a closed region only including the portal vein A3 as a measurement target are displayed on the display unit 8, and the user is prompted to touch either of the inside of the target region line LA1 or the inside of the target region line LA2. Thereby, the user can be prompted to select a measurement target. In this way, the target region line can be displayed for each of a plurality of measurement targets, and the user is prompted to touch the inside of each target region line. Thereby, the user can be prompted to select a measurement target.

A plurality of target region lines displayed on the display unit 8 in this manner can be displayed in different colors. A contour line representing the contour of each measurement target may be displayed instead of the target region line or the inside of each contour line may be displayed in a different color.

In Embodiment 4, although, in a case where a plurality of measurement targets are recognized by the measurement target recognition unit 9, one measurement target is selected by the user through the operating unit 15, a plurality of measurement targets may be selected. For example, the number of measurement targets selectable by the user through the operating unit 15 is set in advance, whereby the measurement target selection reception unit 25 can receive selection of a set number of measurement targets among a plurality of measurement targets.

Embodiment 5

Figure 18:
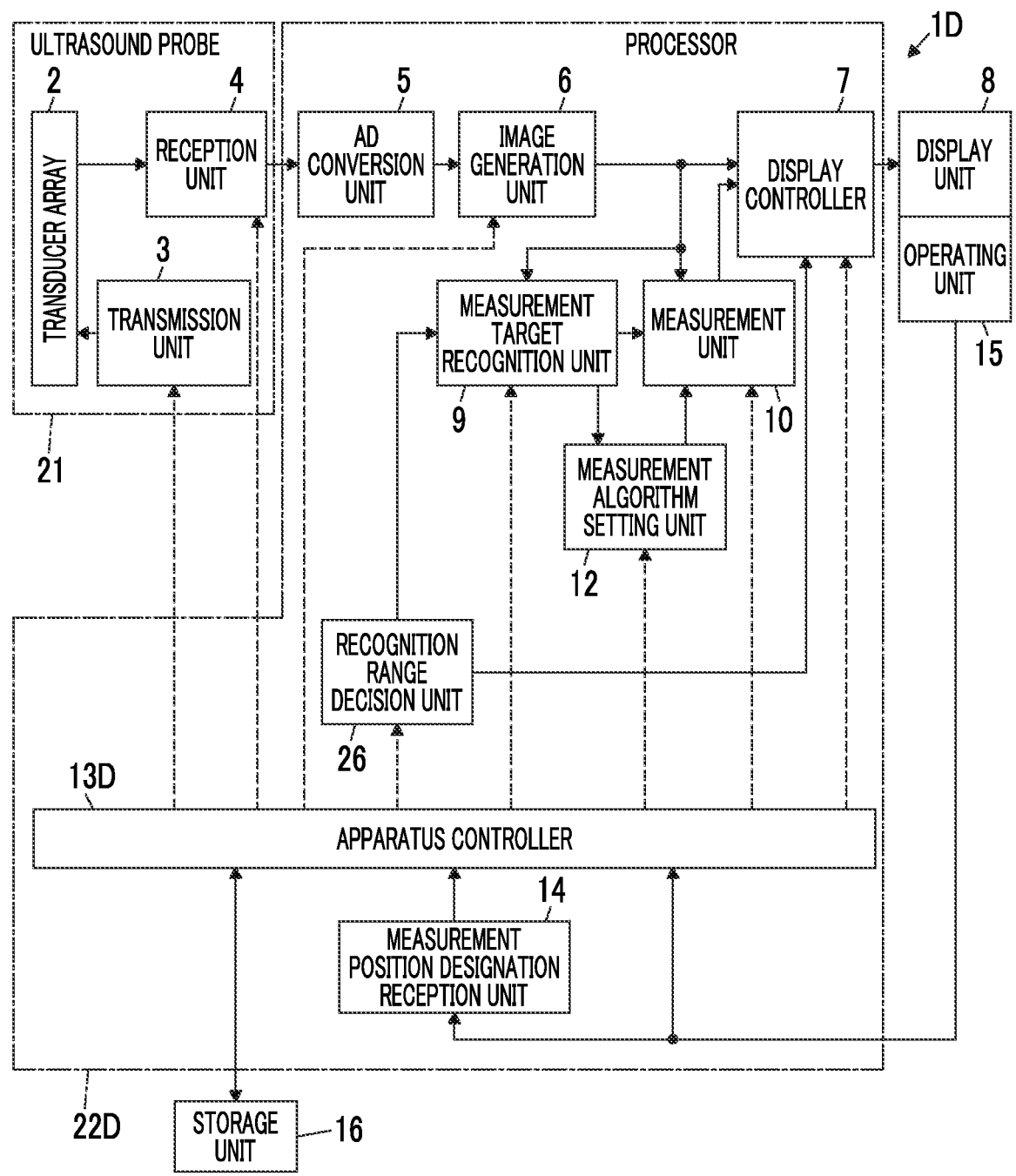
FIG. 18 is a block diagram showing the configuration of an ultrasound diagnostic apparatus according to Embodiment 5 of the invention.

All of the recognition range R1 in Embodiments 1 and 2 and the recognition range R2 in Embodiments 3 and 4 have the determined size. In contrast, the size of the recognition range may be changed by a user's operation through the operating unit 15. FIG. 18 shows the configuration of an ultrasound diagnostic apparatus 1D of Embodiment 5. The ultrasound diagnostic apparatus 1D of Embodiment 5 comprises an apparatus controller 13D instead of the apparatus controller 13 in the ultrasound diagnostic apparatus 1 of Embodiment 1 shown in FIG. 1, and further comprises a recognition range decision unit 26.

In the ultrasound diagnostic apparatus 1D of Embodiment 5, the recognition range decision unit 26 is connected to the measurement target recognition unit 9, and the display controller 7 is connected to the recognition range decision unit 26. The apparatus controller 13D is connected to the transmission unit 3, the reception unit 4, the image generation unit 6, the display controller 7, the measurement target recognition unit 9, the measurement unit 10, the measurement algorithm setting unit 12, the measurement position designation reception unit 14, the operating unit 15, the storage unit 16, and the recognition range decision unit 26.

The AD conversion unit 5, the image generation unit 6, the display controller 7, the measurement target recognition unit 9, the measurement unit 10, the measurement algorithm setting unit 12, the apparatus controller 13C, the measurement position designation reception unit 14, and the recognition range decision unit 26 configure a processor 22D.

The recognition range decision unit 26 of the processor 22D can decide a recognition range after setting the size of the recognition range according to a touch operation with the finger of the user through the operating unit 15. In this case, for example, the recognition range decision unit 26 can decide the size of the recognition range by enlarging and reducing the recognition range having a determined size set in advance according to a touch operation with the finger of the user.

Figure 19:
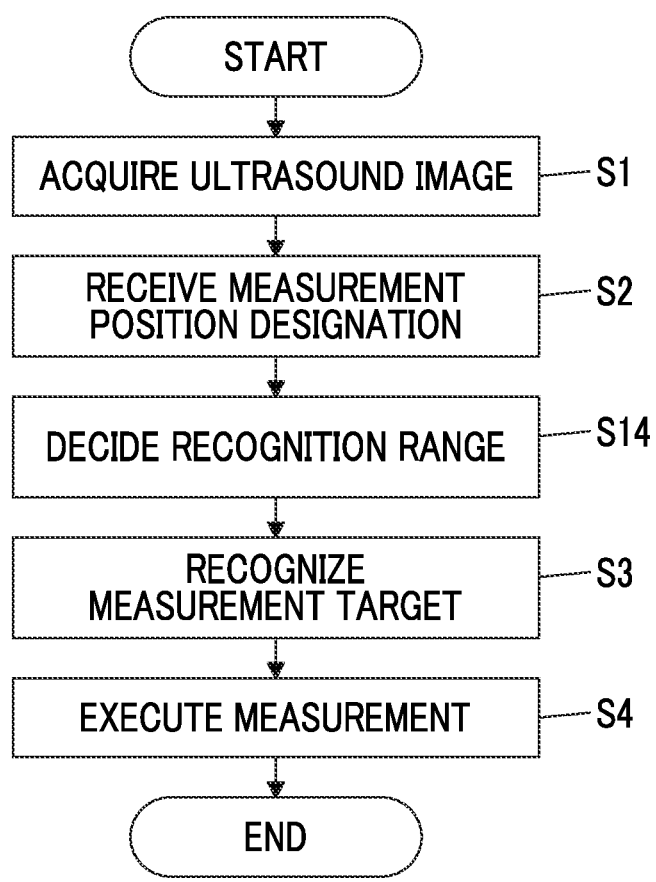
FIG. 19 is a flowchart showing the operation of the ultrasound diagnostic apparatus according to Embodiment 5 of the invention.

Next, the operation of the ultrasound diagnostic apparatus 1D of Embodiment 5 will be described referring to a flowchart shown in FIG. 19. Steps S1 to S4 in the flowchart of FIG. 19 are the same as Steps S1 to S4 in the flowchart shown in FIG. 3, respectively.

Figure 20:
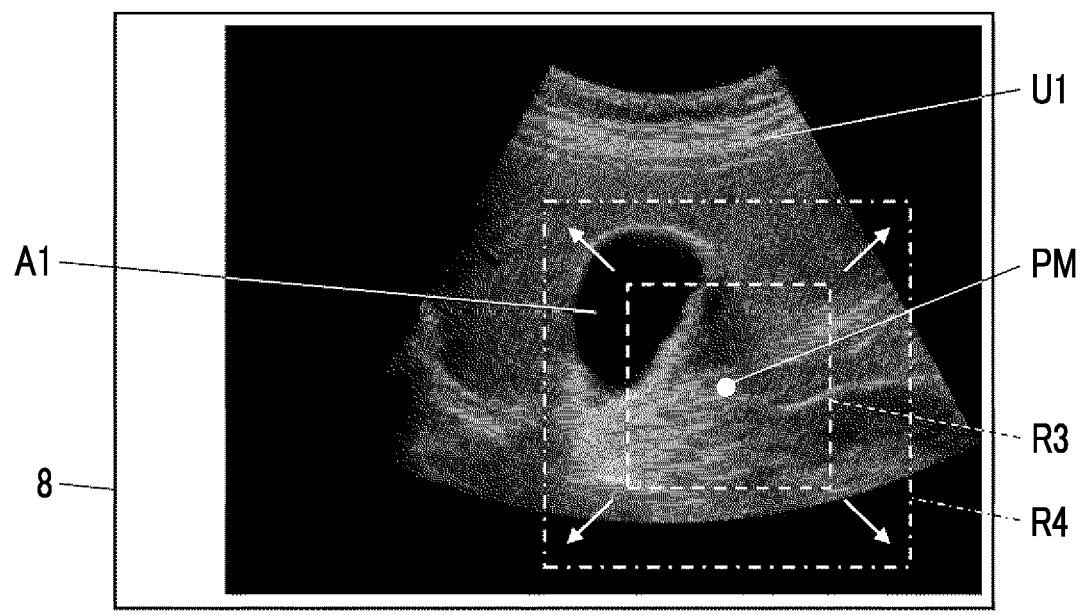
FIG. 20 is a diagram showing an example of a recognition range in Embodiment 5 of the invention.

In Step S1, one ultrasound image U1 is acquired, and as shown in FIG. 20, and an acquired ultrasound image U1 is displayed on the display unit 8.

In Step S2, in a case where the user touches the ultrasound image U1 displayed on the display unit 8 to designate the measurement position PM, the measurement position designation reception unit 14 receives the user's designation of the measurement position PM.

In subsequent Step S14, the recognition range decision unit 26 sets a size of a recognition range according to the touch operation with the finger of the user through the operating unit 15 and decides the recognition range. For example, as shown in FIG. 20, the recognition range decision unit 26 can set a recognition range greater as a time for which the user touches the measurement position PM is longer. FIG. 20 shows a square recognition range R3 in which the measurement position PM is disposed at the center and which has a determined size. While only a part of a region of a gallbladder A1 is included in the recognition range R3, the measurement position PM is continuously touched with the finger of the user, the recognition range R3 is enlarged to a recognition range R4 including the entire region of the gallbladder A1.

When the size of the recognition range is decided in this manner, the recognition range decision unit 26 displays a manner, in which the recognition range is gradually enlarged over time, on the display unit 8 through the display controller 7. In this case, for example, a manner in which, in a case where the measurement position PM is touched with the finger of the user, the recognition range R3 having a predetermined size set as an initial value is displayed on the display unit 8, and the recognition range R3 is gradually enlarged over time until the finger of the user is released from the ultrasound image U2 is displayed on the display unit 8. In a case where the recognition range is enlarged, and the finger of the user is released from the ultrasound image U2 when the recognition range is enlarged to, for example, the recognition range R4, the recognition range R4 is decided as a recognition range in which recognition of a measurement target is performed by the measurement target recognition unit 9.

In this manner, as the recognition range is enlarged, even though the measurement position PM designated by the user is at a position away from an intended measurement target, it is possible to include the intended measurement target in the recognition range.

In subsequent Step S3, the measurement target recognition unit 9 recognizes a measurement target included in the recognition range R4 decided in Step S13. In the example shown in FIG. 20, the gallbladder A1 is included in the recognition range R4, and the measurement target recognition unit 9 can recognize the gallbladder A1.

In subsequent Step S4, automatic measurement of the measurement target recognized in Step S3 is executed, and the operation of the ultrasound diagnostic apparatus 1D ends.

From the above, with the ultrasound diagnostic apparatus 1D of Embodiment 5, when the user touches a position on the ultrasound image U1 to designate the measurement position PM, the longer the time for which the user touches the position on the ultrasound image U with the finger, the greater the recognition range is set. Thus, for example, even though the user designates a position away from an intended measurement target as a measurement position, it is possible to include the intended measurement target in the recognition range, and to reliably execute measurement.

In Embodiment 5, although an example where the recognition range R4 is decided by enlarging the recognition range R3 having the determined size, the recognition range may be reduced.

Figure 21:
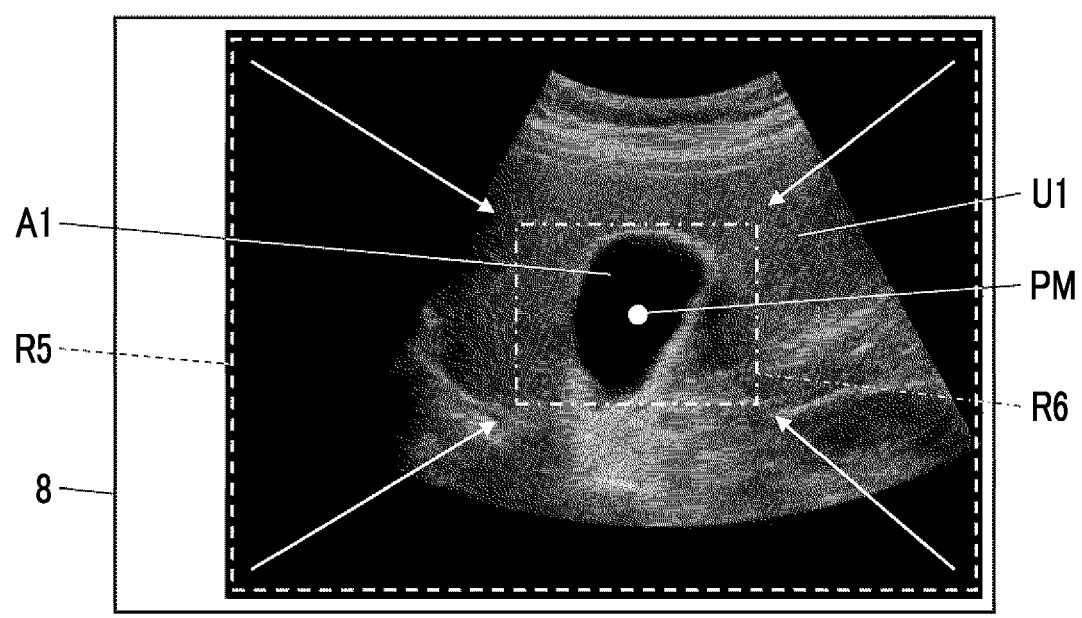
FIG. 21 is a diagram showing an example of a recognition range in a modification example of Embodiment 5 of the invention.

For example, as shown in FIG. 21, the recognition range decision unit 26 may set a recognition range smaller as the time for which the user touches the measurement position PM is longer. In the example shown in FIG. 21, the measurement position PM on the ultrasound image U1 is continuously touched by the user, whereby a recognition range R5 including the entire display region of the ultrasound image U1 on the display unit 8 is reduced to a recognition range R6 only including a gallbladder A1 as a measurement target.

When the size of the recognition range is decided in this manner, the recognition range decision unit 26 displays a manner, in which the recognition range is gradually reduced over time, on the display unit 8 through the display controller 7. In this case, for example, a manner in which in a case where the measurement position PM is touched with the finger of the user, the recognition range R5 including the entire display region of the ultrasound image U1 is displayed on the display unit 8, and the recognition range R5 is gradually reduced until the finger of the user is released from the ultrasound image U1 is displayed on the display unit 8. In a case where the recognition range is reduced, and the finger of the user is released from the ultrasound image U1 when the recognition range is reduced to, for example, the recognition range R6, the recognition range R6 is decided as a recognition range in which recognition of a measurement target is performed by the measurement target recognition unit 9.

In this manner, as the recognition range is reduced, it is possible to set a recognition range to include only a region necessary for recognition of a measurement target intended by the user. With this, it is possible to reduce a calculation load when the measurement target recognition unit 9 performs recognition of a measurement target, thereby prompting the measurement target recognition unit 9 to more promptly recognize a measurement target.

In Embodiment 5, although an example where only one measurement target is included in the ultrasound image U1 has been illustrated, a plurality of measurement targets may be included in the ultrasound image. Such an aspect is realized, for example, by a configuration in which the recognition range decision unit 26 is provided in the ultrasound diagnostic apparatus 1B of Embodiment 3 shown in FIG. 10 and the ultrasound diagnostic apparatus 1C of Embodiment 4 shown in FIG. 16.

Figure 22:
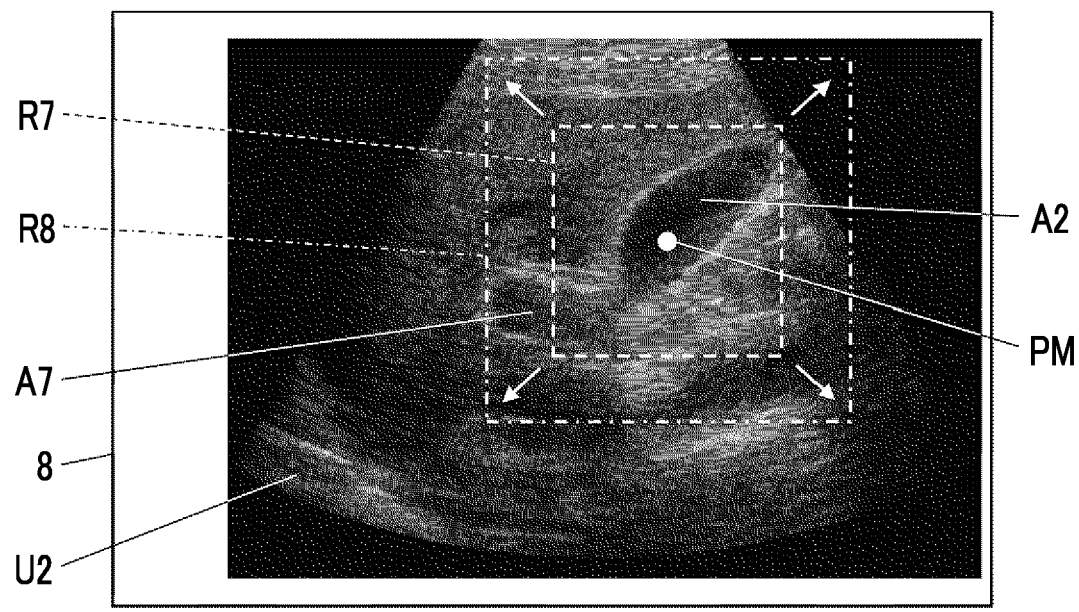
FIG. 22 is a diagram showing an example of a recognition range in another modification example of Embodiment 5 of the invention.

For example, as shown in FIG. 22, a gallbladder A2 and a portal vein A3 are included in the ultrasound image U2, and a measurement position PM on the ultrasound image U2 is continuously touched by the user, whereby a recognition range R7 including a part of the gallbladder A2 and the portal vein A3 can be enlarged to a recognition range R8 including the whole of the gallbladder A2 and the portal vein A3. In this way, with the ultrasound diagnostic apparatus 1D of Embodiment 5, in a case where measurement for a plurality of measurement targets is intended, it is possible to easily include a plurality of intended measurement targets in a recognition range.

Figure 23:
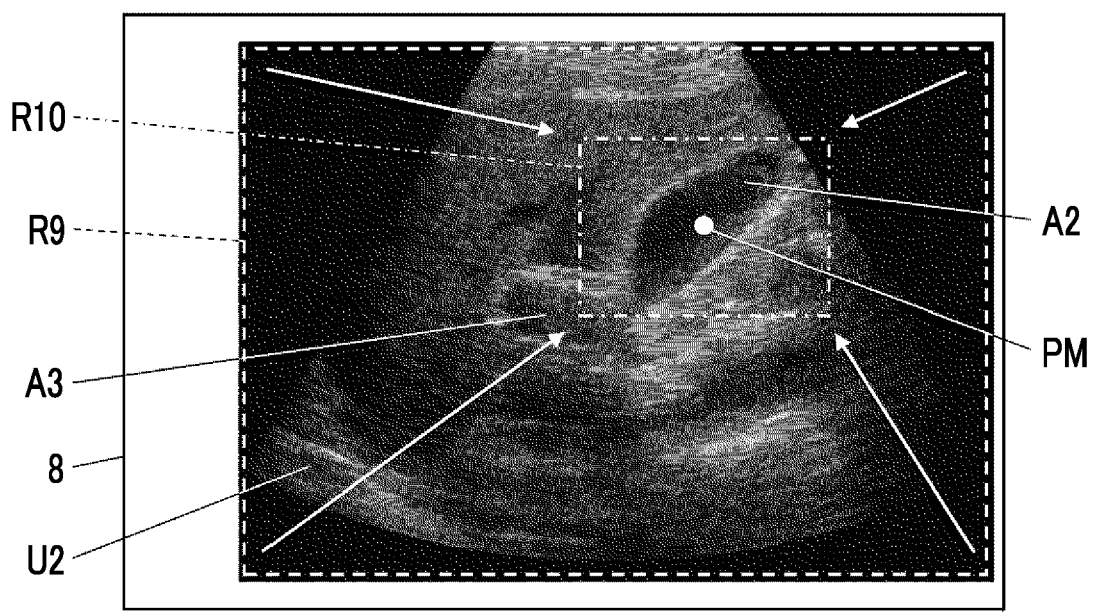
FIG. 23 is a diagram showing an example of a recognition range in still another modification example of Embodiment 5 of the invention.

As shown in FIG. 23, the measurement position PM on the ultrasound image U2 is continuously touched by the user, whereby a recognition range R9 including the entire display region of the ultrasound image U2 on the display unit 8 may be reduced to a recognition range R10 only including the gallbladder A2 as a measurement target. In this manner, the recognition range is reduced, whereby it is possible to set a recognition range to include a measurement target intended by the user. With this, it is possible to reduce a calculation load when the measurement target recognition unit 9 performs recognition of a measurement target, thereby prompting the measurement target recognition unit 9 to more promptly recognize a measurement target.

As described above, although, when the user touches the position on the ultrasound image to designate the measurement position PM, the recognition range decision unit 26 can set the size of the recognition range according to the time for which the user touches the position on the ultrasound image with the finger, an aspect of setting a size of a recognition range is not limited thereto.

For example, in a case where the measurement position PM is designated by the user touching the display screen of the display unit 8 with the finger to overlap the ultrasound image, and the user moves the finger while touching the display screen with the finger, the recognition range decision unit 26 can set the size of the recognition range according to a movement direction and a movement distance of the finger of the user on the ultrasound image. For example, in a case where the user moves the finger to the right while touching the display screen of the display unit 8 with the finger, the recognition range decision unit 26 can gradually enlarge the recognition range according to a movement distance, and in a case where the user moves the finger to the left while touching the display screen of the display unit 8 with the finger, the recognition range decision unit 26 can gradually reduce the recognition range according to a movement distance. Here, the movement direction of the finger of the user for enlarging and reducing the recognition range is not limited to the right-left direction, and can be set to any direction, such as an up-down direction or an oblique direction.

With this, the recognition range decision unit 26 can easily set the size of the recognition range to the size of the recognition range according to the purpose of the user.

Though not shown, for example, as the operating unit 15 is provided with a pressure sensor disposed to be superimposed on the display unit 8 and the touch sensor, the recognition range decision unit 26 can set the size of the recognition range according to magnitude of pressure of the finger of the user detected by the pressure sensor. In this case, the recognition range decision unit 26 can enlarge the recognition range as the pressure detected by the pressure sensor increases. Alternatively, the recognition range decision unit 26 can reduce the recognition range as the pressure detected by the pressure sensor increases.

In Embodiments 1 to 5, although the operating unit 15 comprises the touch sensor, the configuration of the operating unit 15 is not limited thereto. For example, as the operating unit 15, an interface through which the user performs an input operation, such as a keyboard, a mouse, or a trackball, can be used.

In Embodiments 1 to 5, although the measurement of the measurement target is executed based on the ultrasound image, measurement of a measurement target can be executed on an acoustic wave image other than an ultrasound image. For example, measurement of a measurement target can be executed on a photoacoustic wave image and a composite image in which an ultrasound image and a photoacoustic wave image are superimposed.

EXPLANATION OF REFERENCES 1, 1A, 1B, 1C, 1D: ultrasound diagnostic apparatus
2: transducer array
3: transmission unit
4: reception unit
5: AD conversion unit
6: image generation unit
7: display controller
8: display unit
9: measurement target recognition unit
10: measurement unit
12: measurement algorithm setting unit
13, 13A, 13B, 13C, 13D: apparatus controller
14: measurement position designation reception unit
15: operating unit
16: storage unit
17: signal processing unit
18: DSC
19: image processing unit
21: ultrasound probe
22, 22A, 22B, 22C, 22D: processor
23: measurement execution instruction reception unit
24: measurement order decision unit
25: measurement target selection reception unit
26: recognition range decision unit
A1, A2: gallbladder
A3: portal vein
C1A, C1B, C2A, C2B, C3A, C3B, C4A, C4B: caliper
LA1, LA2: target region line
LT: measurement target list
ML1, ML2, ML3, ML4: measurement line
PM: measurement position
PR: measurement result panel
R1, R2, R3, R4, R5, R6, R7, R8, R9, R10: recognition range
U1, U2: ultrasound image

What is claimed is:

1. An acoustic wave diagnostic apparatus comprising:
a monitor configured to display an acquired acoustic wave image, the monitor further including a touch sensor, wherein the touch sensor is superimposed on the monitor;
a memory configured to store, in advance, a plurality of measurement algorithms each of which is specialized for each of a plurality of organs of a subject, where the plurality of measurement algorithms define measurement groups each of which includes at least one measurement item, and a number of measurement items, types of measurement items or a combination of measurement items is different from each other between any pair of measurement algorithm among the plurality of measurement algorithms; and
a processor configured to
set a first range including a whole of the acoustic wave image,
receive, via the touch sensor from a user, designation of a measurement position on the acoustic wave image displayed on the monitor,
reduce the first range such that the first range becomes smaller as a time where the measurement position is touched by the user through the touch sensor is longer and the first range includes the measurement position,
set the reduced first range as a recognition range,
recognize a measurement target included in the acoustic wave image of the recognition range as one organ among the plurality of organs,
uniquely select and set a first measurement algorithm specialized for the measurement target recognized, from the plurality of measurement algorithms, by referring to the memory, and
automatically execute one or more measurement items included in a measurement group of the first measurement algorithm for the measurement target on the acoustic wave image and display a measurement result on the monitor.

2. The acoustic wave diagnostic apparatus according to claim 1,
wherein upon receipt of the measurement position, the processor is configured to automatically perform the recognition of the measurement target, the setting of the first measurement algorithm, and the measurement of the measurement target and the display of the measurement result, sequentially.

3. The acoustic wave diagnostic apparatus according to claim 1, wherein the processor is configured to
receive an instruction to start the measurement of the measurement target issued by the user, and
by using the instruction as a trigger, automatically perform the recognition of the measurement target, the setting of the first measurement algorithm, and the measurement of the measurement target and the display of the measurement result, sequentially.

4. The acoustic wave diagnostic apparatus according to claim 1,
wherein upon recognition of a plurality of the measurement targets in the recognition range, the processor is configured to
uniquely select and set measurement algorithms specialized for the plurality of the measurement targets, from the plurality of measurement algorithms, by referring to the memory, and
measure each of the plurality of the measurement targets and display a measurement result of each measurement target on the monitor.

5. The acoustic wave diagnostic apparatus according to claim 2,
wherein upon recognition of a plurality of the measurement targets in the recognition range, the processor is configured to
uniquely select and set measurement algorithms specialized for the plurality of the measurement targets, from the plurality of measurement algorithms, by referring to the memory, and
measure each of the plurality of the measurement targets and display a measurement result of each measurement target on the monitor.

6. The acoustic wave diagnostic apparatus according to claim 3,
wherein upon recognition of a plurality of the measurement targets in the recognition range, the processor is configured to
uniquely select and set measurement algorithms specialized for the plurality of the measurement targets, from the plurality of measurement algorithms, by referring to the memory, and
measure each of the plurality of the measurement targets and display a measurement result of each measurement target on the monitor.

7. The acoustic wave diagnostic apparatus according to claim 4,
wherein the processor is configured to display the measurement results of the plurality of the measurement targets on the monitor in association with the plurality of the measurement targets on the acoustic wave image, respectively.

8. The acoustic wave diagnostic apparatus according to claim 5,
wherein the processor is configured to display the measurement results of the plurality of the measurement targets on the monitor in association with the plurality of the measurement targets on the acoustic wave image, respectively.

9. The acoustic wave diagnostic apparatus according to claim 6,
wherein the processor is configured to display the measurement results of the plurality of the measurement targets on the monitor in association with the plurality of the measurement targets on the acoustic wave image, respectively.

10. The acoustic wave diagnostic apparatus according to claim 4,
wherein upon recognition of the plurality of the measurement targets in the recognition range, the processor is configured to
decide a measurement order of the plurality of the measurement targets,
set the measurement algorithms sequentially for the plurality of the measurement targets in compliance with the measurement order decided, and
measure the plurality of measurement targets sequentially from the measurement target, for which the measurement algorithms are set, and display measurement results of the plurality of the measurement targets on the monitor.

11. The acoustic wave diagnostic apparatus according to claim 7, wherein upon recognition of the plurality of the measurement targets in the recognition range, the processor is configured to
- a measurement order of the plurality of the measurement targets,
- the measurement algorithms sequentially for the plurality of the measurement targets in compliance with the measurement order decided, and
- measure the plurality of measurement targets sequentially from the measurement target, for which the measurement algorithms are set, and display measurement results of the plurality of the measurement targets on the monitor.

12. The acoustic wave diagnostic apparatus according to claim 10,
wherein the processor is configured to provide the measurement order to the plurality of the measurement targets such that the shorter a distance from the measurement position on the acoustic wave image is, the earlier the measurement order becomes.

13. The acoustic wave diagnostic apparatus according to claim 4,
wherein upon recognition of the plurality of the measurement targets in the recognition range, the processor is configured to
- receive selection of one measurement target among the plurality of the measurement targets from the user,
- set the first measurement algorithm specialized for the one measurement target of which the selection is received, and
- measure the one measurement target based on the first measurement algorithm and display a measurement result on the monitor.

14. The acoustic wave diagnostic apparatus according to claim 1, further comprising:
a touch sensor disposed to be superimposed on the monitor;
wherein the processor is configured to receive a position touched with a finger of the user on the acoustic wave image displayed on the monitor as the measurement position.

15. The acoustic wave diagnostic apparatus according to claim 1,
wherein the recognition range has a determined size.

16. The acoustic wave diagnostic apparatus according to claim 14,
wherein the processor is configured to set the size of the recognition range according to a touch operation with the finger of the user.

17. The acoustic wave diagnostic apparatus according to claim 16,
wherein the processor is configured to set the size of the recognition range according to a length of a time for which the measurement position on the acoustic wave image is touched with the finger of the user.

18. The acoustic wave diagnostic apparatus according to claim 16,
wherein the processor is configured to set the size of the recognition range according to a movement direction and a movement distance of the finger of the user on the acoustic wave image in a case where the measurement position of the acoustic wave image is touched with the finger of the user and the finger of the user is moved on the acoustic wave image.

19. An acoustic wave diagnostic apparatus comprising:
a monitor configured to display an acquired acoustic wave image, the monitor further including a touch sensor, wherein the touch sensor is superimposed on the monitor;
a memory configured to store, in advance, a first measurement algorithm which is specialized for a gallbladder and a second measurement which is specialized for a kidney, where the first measurement algorithm defines to measure a length of a longest line segment having two points on an inner wall of the gallbladder included in the acoustic wave image as end points and passing through a center point of the gallbladder, and the second measurement algorithm defines to measure a distance between two points which are farthest from each other on a contour of the kidney included in the acoustic wave image; and
a processor configured to
- set a first range including a whole of the acoustic wave image,
- receive, via the touch sensor from a user, designation of a measurement position on the acoustic wave image displayed on the monitor,
- reduce the first range such that the first range becomes smaller as a time where the measurement position is touched by the user through the touch sensor is longer and the first range includes the measurement position,
- set the reduced first range as a recognition range,
- recognize a measurement target included in the acoustic wave image of the recognition range as one of the gallbladder and the kidney,
- uniquely select and set one measurement algorithm of the first measurement algorithm and the second measurement algorithm specialized for the recognized measurement target, by referring to the memory, and
- measure the measurement target on the acoustic wave image based on the one measurement algorithm and display a measurement result on the monitor.

* * * * *